(12) United States Patent
Cheng et al.

(10) Patent No.: US 6,306,899 B1
(45) Date of Patent: Oct. 23, 2001

(54) INHIBITION AND TREATMENT OF HEPATITIS B VIRUS AND FLAVIVIRUS BY HELIOXANTHIN AND ITS ANALOGS

(75) Inventors: Yung-Chi Cheng, Woodbridge, CT (US); Chen-Kung Chou, Taipei (TW); Lei Fu, Hamilton (CA); Yueh-Hsiung Kuo; Sheau-Farn Yeh, both of Taipei (TW); Juliang Zhu, Hamden; Yonglian Zhu, New Haven, both of CT (US)

(73) Assignees: Yale University, New Haven, CT (US); N. Y. Mu, N.T.U., V.G.H, Taipei (TW)

( * ) Notice: Subject to any disclaimer, the term of this patent is extended or adjusted under 35 U.S.C. 154(b) by 0 days.

(21) Appl. No.: 09/379,050

(22) Filed: Aug. 23, 1999

Related U.S. Application Data
(60) Provisional application No. 60/098,025, filed on Aug. 25, 1998.

(51) Int. Cl.[7] ................................................ A61K 31/36
(52) U.S. Cl. .................. 514/464; 514/467; 514/569; 514/729; 514/935; 549/235; 549/320; 549/433; 562/466; 568/808
(58) Field of Search .................................... 549/235, 320, 549/433; 514/464, 467, 569, 729, 935; 562/466; 568/808

(56) References Cited

U.S. PATENT DOCUMENTS

| | | | |
|---|---|---|---|
| 4,486,445 | 12/1984 | Patel et al. | 424/279 |
| 4,673,575 | 6/1987 | Venkateswaran et al. | 424/195.1 |
| 4,937,074 | 6/1990 | Venkateswaran et al. | 424/195.1 |
| 4,999,428 | 3/1991 | Saksena et al. | 544/277 |
| 5,015,739 | 5/1991 | Saksena et al. | 544/277 |
| 5,070,103 | 12/1991 | Iwasaki et al. | 514/463 |
| 5,684,010 | * 11/1997 | Schinazi et al. | 514/266 |
| 5,726,174 | 3/1998 | Kim et al. | 544/244 |
| 5,777,116 | 7/1998 | Onishi et al. | 544/264 |
| 5,817,638 | 10/1998 | Hostetler | 514/45 |
| 5,821,242 | 10/1998 | Colacino et al. | 514/227.2 |
| 5,830,881 | 11/1998 | Lin et al. | 514/45 |
| 5,834,507 | 11/1998 | Gordaliza et al. | 514/463 |
| 5,837,871 | 11/1998 | Kim et al. | 544/243 |
| 5,891,874 | 4/1999 | Colacino et al. | 514/234.5 |
| 5,925,512 | 7/1999 | Carman et al. | 435/5 |

FOREIGN PATENT DOCUMENTS

| | | |
|---|---|---|
| 61-215394 | 9/1986 | (JP) . |
| WO9807437 | 2/1998 | (WO) . |

OTHER PUBLICATIONS

Ott et al. "Phyllanthus amarus suppresses hepatitis B virus by interrupting interactions between HBV enhancer I and cellular transcription factors"; *European journal of Clinical Investigation* 27(11):908–15, Nov. 1997.

Kuo, "Studies on several naturally occurring lignans"; *Kaohsiung Journal of Medical Sciences* 5(11):621–4, Nov. 1989.

He et al. "Bioactive compounds from Taiwania cryptomerioides" *Journal of Natural Products*, 60(1):38–40, 1997.

Swoboda, G.A. Phytochemical Studies. Part V. The Synthesis of Taiwanin A. J. Chem. Soc. (C), 1967, p. 161–162.

Momose T. et al. Chem. abstr. vol. 90, No. 13, Mar. 26, 1979, the abstract No. 103877d. "Synthetic Studies on Lignans and Related Compounds VII Synthesis If Justicidin B and Diphyllin and of Taiwanin C and E from 2,3–dibenzylidenebutyrolactones via β–apolignans: a Chemical Model for Natural Co–ocurrence of 4–hydrogen– and 4–hydrosy–1–phenyl–2,3–naphthalides in Plants", Chem. Pharm. Bull., 1978, 26(10), p. 3195–3198.

Tanaka M. et al. Chem. abstr., vol. 123, No. 17, Oct. 23, 1995, the abstract No. 227979h. "Preparation of Tetrahydronaphthalene Derivative and Retrovirus Infection Remedy Containing the Same as Active Ingredient", PCT Int'l Appl. WO 95 01, 950.

* cited by examiner

*Primary Examiner*—Amelia Owens
(74) *Attorney, Agent, or Firm*—Coleman Sudol Sapone, P.C; Henry D. Coleman; R. Neil Sudol

(57) ABSTRACT

This invention relates to anti-viral drugs such as Helioxanthin and its analogs. The present compounds may be used alone or in combination with other drugs for the treatment of Hepatitis B virus (HBV), Hepatitis C virus (HCV), Yellow Fever, Dengue Virus, Japanese Encephalitis, West Nile virus and related flaviviruses. In addition, compounds according to the present invention can be used to prevent hepatoma secondary to virus infection as well as other infections or disease states which are secondary to the virus infection.

51 Claims, 10 Drawing Sheets

ZHU-IX-139-1
NO. 145 HELIOXANTHIN
MW: 348.3

ZHU-IX-139-2
RETROHELIOXANTHIN
MW: 348.3

ZHU-IX-143
8,2'-DIBROMO-HELIOXANTHIN
MW: 506.1

ZHU-IX-124-2
MW: 352.33

ZHU-IX-135-1
MW: 431.23

ZHU-IX-122-1
MW: 336.33

ZHU-IX-120-1
MW: 520.08

ZHU-IX-120-2
MW: 520.08

ZHU-IX-120-3
MW: 441.18

ZHU-IX-157
MW: 388.3

ZHU-IX-153
MW: 388.3

ZHU-IX-159
MW: 336.33

ZHU-IX-163-2
MW: 320.33

ZHU-IX-189
MW 334.31

ZHU-X-4
MW 350.31

Structures of Helioxanthin and its derivatives II

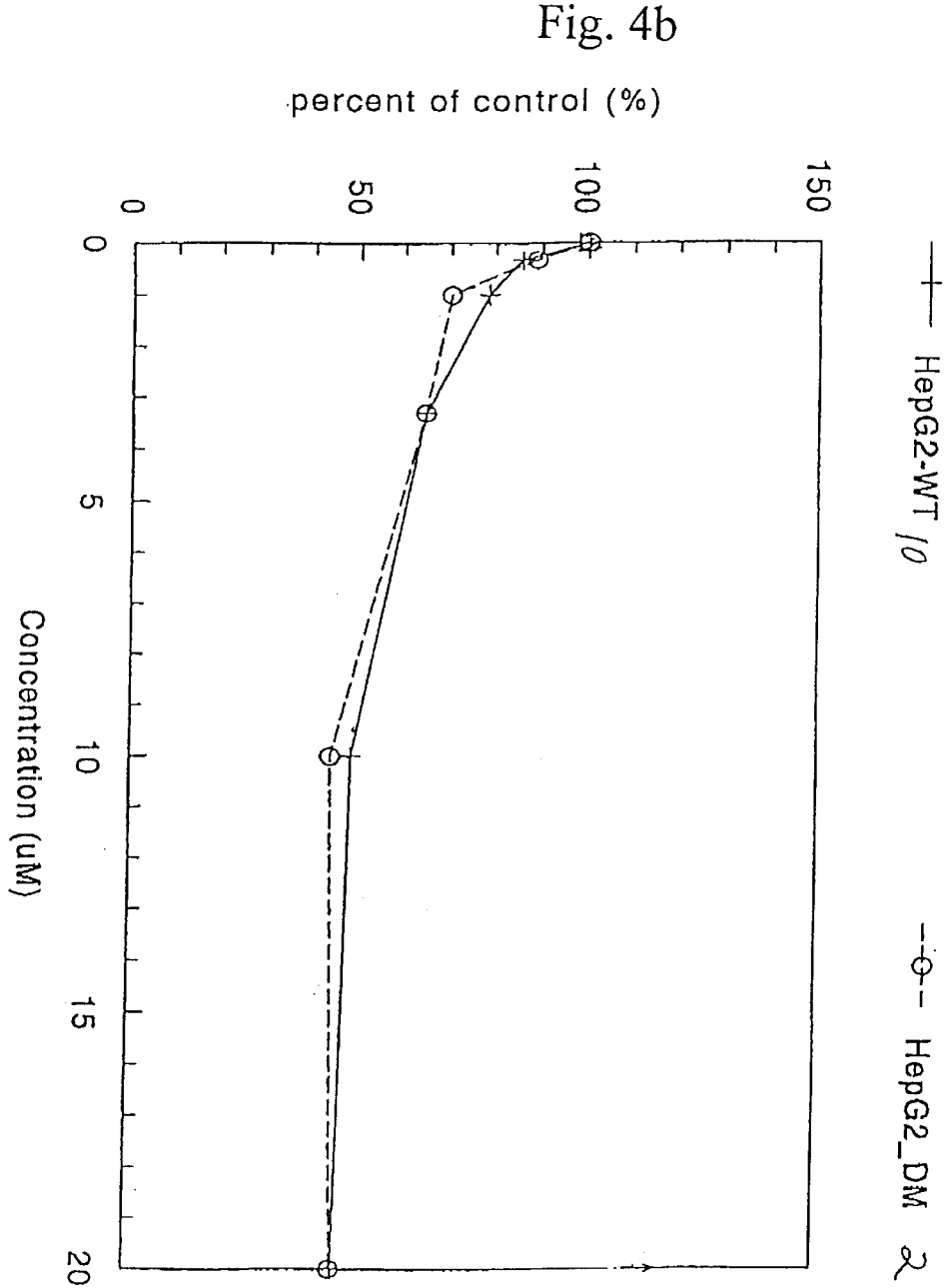

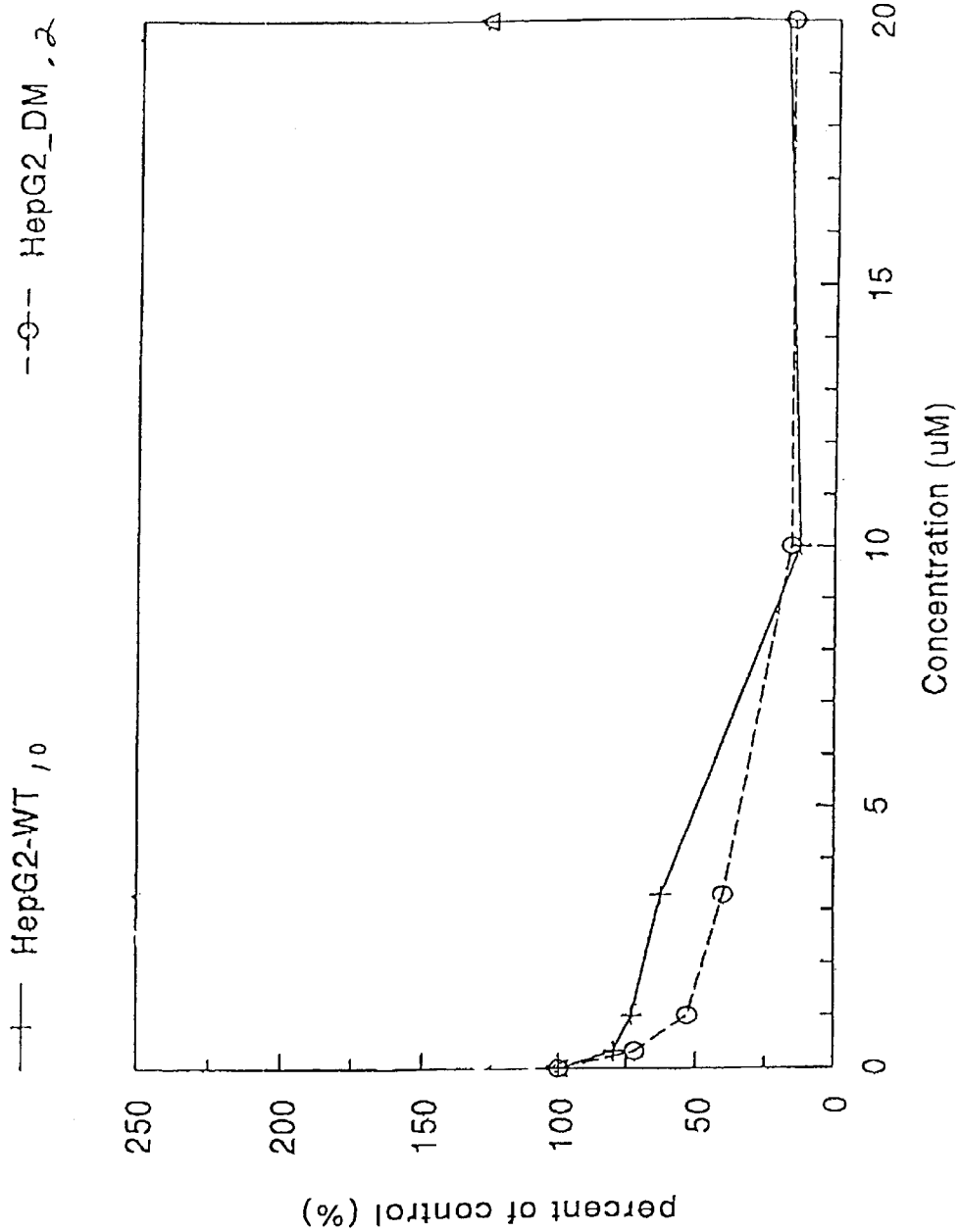

INHIBITION AND TREATMENT OF HEPATITIS B VIRUS AND FLAVIVIRUS BY HELIOXANTHIN AND ITS ANALOGS

RELATED APPLICATIONS

This application claims priority from provisional application No. 60/098,025, filed Aug. 25, 1998.

FIELD OF THE INVENTION

This invention relates to the anti-viral drugs such as Helioxanthin and its analogs compounds. These compounds may be used alone or in combination with other drugs for the treatment of the following: Hepatitis B virus (HBV), Hepatitis C virus (HCV), Yellow Fever, Dengue Virus, Japanese Encephalitis, West Nile virus and related flaviviruses. In addition, compounds according to the present invention can be used to prevent hepatoma secondary to virus infection as well as other infections or disease states which are secondary to the virus infection.

BACKGROUND OF THE INVENTION

Hepatitis B virus infection is a major health problem worldwide. HBV is a causative agent of both an acute and chronic form of hepatitis. More than 300 million people throughout the world are chronic carriers of HBV. Typically, the human host is unaware of infection and HBV infection leads to acute hepatitis and liver damage, abdominal pain, jaundice and elevated blood levels of certain enzymes. Additionally, HBV contributes to the formation of hepatocellular carcinoma and is second only to tobacco as a cause of human cancer. The mechanism by which HBV induces cancer is unknown, although it has been postulated that it may directly trigger tumor development or indirectly trigger tumor formation through chronic inflammation, cirrhosis and cell regeneration associated with the infection.

HBV belongs to the genus of hepadnavirus in the hepadnaviridae family. The genome of HBV consists of circular, partially double-stranded DNA of about 3200 base pairs that code for seven viral proteins. The polymerase gene completely overlaps the viral envelope genes PreS1, PreS2 and S and partially overlaps the X and core genes. The envelope of HBV consists of three proteins and their glycosylated derivatives. The three proteins, the small (S), middle (M) and large (L), are hepatitis B surface (HBs) proteins that contain the S gene sequence. Other proteins such as the MHBs contain the PreS2 sequence.

The core gene contains the nucleocapsid protein (183–185 aa) and the hepatitis B core antigen. The precore region, upstream of the core region, consists of 87 nucleotides that codes for 29 amino acids and is in phase with the core region. The first 19 amino acids of the precore region act as a signal for membrane translocation and eventual secretion of the precore gene product, the Hbe antigen.

Although a DNA virus, HBV requires reverse transcription through the formation of a (+) strand RNA intermediate. Reverse transcriptase has poor proof-reading ability and this leads to a high rate of nucleotide misincorporation; calculations suggest that this error-prone replication leads to one point replacement, deletion or insertion per 1000 to 100,000 nucleotides copied.

Additionally, other mutations in the precore, core and in the PreS and S, also give Hepatitis B virus a selective advantage in acquiring drug resistance.

The best defense to date has been vaccination. Human serum-derived vaccines, through genetic engineering, have been developed. Although the vaccine has been found effective, production has been hampered by the limited supply of human serum from chronic carriers and a long and expensive purification process. Furthermore, each batch of vaccine must be tested in chimpanzees to ensure safety. Additionally, vaccines do not help the patients already infected with the virus.

Great efforts have been made to develop clinically useful treatments for hepatitis B but they have been met with limited success. For example, interferon and several nucleoside analogs have shown relatively low cure rate of hepatitis B and they have often produced serious adverse effects. 2',3'-dideoxycytidine (ddC) has had high toxicity on the central and peripheral nervous system. Another nucleoside analog, ara-AMP, was found to transiently suppress HBV infection but also has been shown to be extremely toxic as well.

Cyclopentyl purine derivatives have also shown anti-viral activity. The process for preparing such compositions have been disclosed in U.S. Pat. Nos. 4,999,428 and 5,015,739. Additionally, Onishi et al., in U.S. Pat. No. 5,777,116 have disclosed a method of making cyclopropane derivatives that include a xanthin-9-yl group.

Schinazi et al., in U.S. Pat. No. 5,684,010, have produced enantiontiomerically pure beta-D-dioxolane nucleosides which show selective anti-hepatitis B activity. Additionally, Lin et al., in U.S. Pat. No. 5,830,881, have discovered that certain dideoxynucleoside analogs which contain a ribofuranosyl moiety having a L-configuration instead of the usual D-configuration showed potent inhibition of viral replication. However, unlike other nucleoside analogs, these analogs have shown very low toxicity to the host cells such as animal or human.

In the past, anti-HBV nucleotide analogs such as 3TC, PCMEA, amd PCV have been used in clinical trials. However, some HBV-infected patients often experience a recurrence of HBV after a period of treatment with 3TC or PCV; this recurrence is due to the emergence of viral resistance. Additionally, the 3TC-resistant HBV, for example, becomes cross-resistant to other anti-HBV nucleotide analogs.

Hostetler, in U.S. Pat. No. 5,817,638, have produced nucleoside analogs such as 2',3'-dideoxycytosine, which are liked through a 5' phosphate of the pentose group to selected lipids such as dioleoylphosphatidylcholine. The lipophilic nature provides an advantage over the use of the nucleoside analog alone and makes it possible to incorporate them into the lamellar structure of liposomes. This form enables them to be taken up by liver cells which harbor the hepatitis B virus.

Processes have been disclosed by Holly et al., in U.S. Pat. Nos. 5,142,051, 5,641,763 and 5,869,467 for the production of N-(2-phosphonylmethoxyethyl) and N-(3-hydroxy-2-phosphonylmethoxypropyl) derivatives of pyrimidine and purine bases. These compounds also could include a xanthin-9-yl group. These compounds are regarded as acyclic analogues of nucleosides in which the nucleoside sugar moiety is replaced by a substituted carbon chain bearing hydroxy groups.

Although the compounds developed by Holly and others have not been tested specifically against hepatitis B viruses, they have shown in-vitro anti-viral activity against other DNA viruses such as the herpes viruses. Other analogs that show anti-Hepatitis B virus activity include phosphonomethyoxymethyl purine and pyrimidine derivatives as described by Kim et al in U.S. Pat. Nos. 5,726,174 and 5,837,871.

Chang et al., on the other hand, in U.S. Pat. No. 5,929,038, have developed an anti-HBV compound that is an iridoid aglycone compound produced from the parent iridoid glycosides which are monoteropenoid compounds and are derived from medicinal plants. In addition to inhibiting HBV DNA synthesis, these compounds also protect the liver from hepatic damage isuch as that induced by carbon tetrachloride intoxication.

In the past, anti-HBV nucleotide analogs such as 3TC (L(-)SddC), PCMEA, amd PCV have been used in clinical trials. However, some HBV-infected patients often experience a recurrence of HBV after a period of treatment with 3TC or PCV; this recurrence is due to the emergence of viral resistance. Additionally, the 3TC-resistant HBV, for example, becomes cross-resistant to other anti-HBV nucleotide analogs.

Flaviviruses belong to the genus Flavivirus of the family Togaviridae. According to virus taxonomy, about 50 viruses including Hepatitis C virus (HCV), Yellow Fever virus, Dengue Virus, Japanese Encephalitis virus, West Nile virus and related flaviviruses. The viruses belonging to the genus Flavivirus are simply called flaviviruses.

The flaviviruses are agents of infectious disease and predominate in East, Southeast and South Asia and Africa, although they may be found in other parts of the world as well. Japanese encephalitis virus is the causative agent of Japanese encephalitis (JE). The mortality rate from JE is rather high and the disease brings heavy sequelae. Although found in Japan, the disease has spread to other parts of Asia and is now found predominantly outside of Japan, primarily in South and Southeast Asia.

Dengue viruses are causative agents of dengue fever/dengue hemorrhagic fever. Infection with dengue viruses is a major public health problem in tropical countries, expecially in Southeast Asia and the Western Pacific, but dengue viruses may also be found in the Americas. As the dengue virus is transmitted to humans via the *Aedes aegypti* mosquito, it is not unexpected that the tropical and subtropical countries, in particular, those in Southeast Asia are highly endemic for dengue.

A major concern and increasing problem for public health officials has been the occurrence of severe complications which arise from dengue viral infections. Both dengue hemorrhagic fever (DHF) and shock syndrome (DSS) are clinical outcomes related to the presence of pre-existing immunity to a heterologous dengue virus serotype. Dengue hemorrhagic fever is initially characterized by a minor febrile illness lasting approximately 3–5 days. The patient may deteriorate at defervescence into the next phase of the syndrome with hemostatic disorders and increased vascular permeabilty frequently accompanied by internal bleeding and shock. As many as 1.5 million children are reported to have been hospitalized with 33,000 deaths from this syndrome since it was first recognized in Thailand in the 1950's. DHF/DSS has since continued to persist in South Asia. DHS/DSS is also found in a number of tropical or near tropical countries, including Cuba, Burma, Indonesia, India, Maldives, Sri Lanka and the South Pacific Islands. Dengue outbreaks are usually associated with a density of mosquito vectors, in particular, *Aedes aegypti*.

Dengue viruses can be divided into 4 serotpyes which are antigenically very similar to each other, but which differ enough to elicit only partial cross-protection after infection by one serotype. Such an infection by one serotype therefore, does not provide life-long immunity to the other serotypes. Vaccine approaches to preventing dengue infections have been unsuccessful to date.

Acute viral hepatitis is a disease which many result in chronic liver damage. It is clinically diagnosed by a well-defined set of patient symptoms, including jaundice, hepatic tendrness and an increase in the serum levels of alanine aminotransferase and aspartate aminotransferase. For many years, the agent of non-A, non-B hepatitis (NANBH) remained elusive. It has now been established that many cases of NANBH are caused by a distinct virus termed hepatitis C virus (HCV).

Colacino et al. in U.S. Pat. Nos. 5,821,242 and 5,891,874, have developed a series of benzimidazaole compounds which inhibit replication in other flaviviruses such as Hepatitis C by interfering with the structure and function of the viral replication complex.

To this date, no such research has involved the development of anti-HBV compounds from the helioxanthin class. Helioxanthin No. 145 has been isolated from the plant, *Taiwaia cryptomeriodides*.

OBJECTS OF THE INVENTION

It is an object of the present invention to provide compounds, medicaments including pharmaceutical compositions and methods of treating and/or preventing infections from Hepatitis B virus (HBV), Hepatitis C virus (HCV), Yellow Fever virus, Dengue Virus, Japanese Encephalitis, West Nile virus and related flaviviruses and related conditions and/or disease states in patients.

It is an additional object of the present invention to provide, in certain embodiments a method of preventing the formation of HBV or HCV related heptatoma in patients exposed to HBV or HCV or who have an HBV or HCV infection.

It is still a further object of the present invention to provide a method of treating 3TC (L(-)SddC) resistant HBV infections

BRIEF DESCRIPTION OF THE INVENTION

Figure 1A:
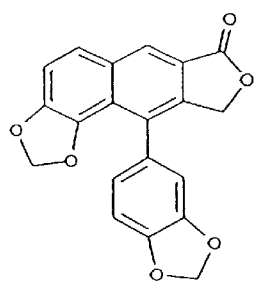
FIGS. 1A, 1B and 1C represent the chemical structures of Helioxanthin and related analogs of the present invention.
Figure 1A:
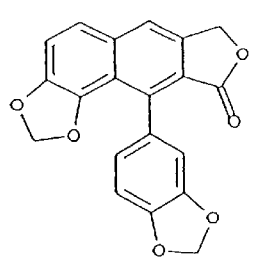
Figure 1A:
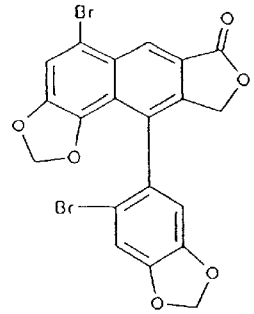
Figure 1A:
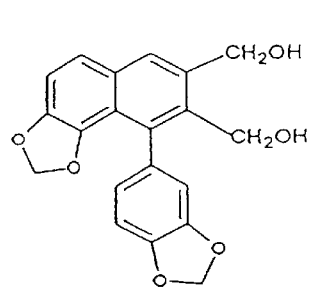
Figure 1A:
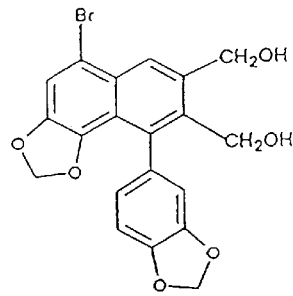
Figure 1A:
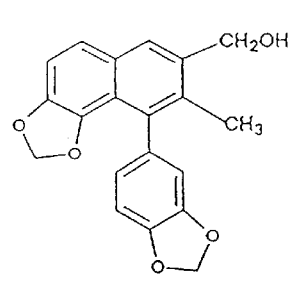
Figure 1A:
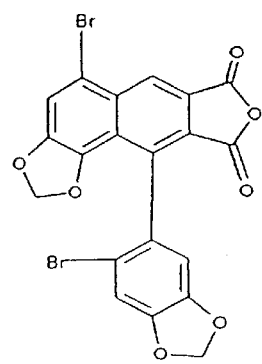
Figure 1A:
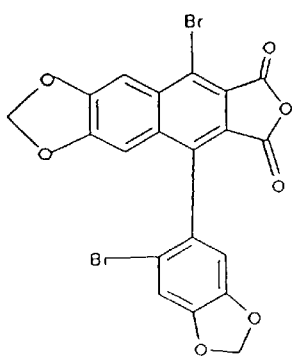
Figure 1A:
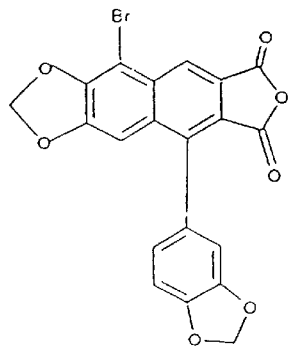
Figure 1B:
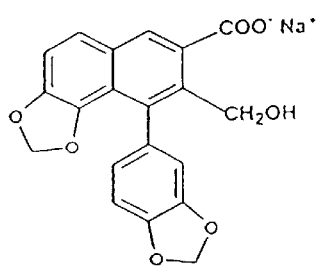
Figure 1B:
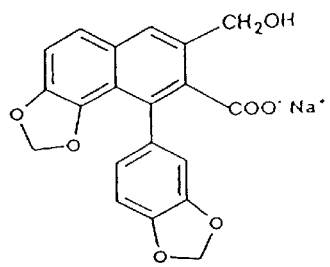
Figure 1B:
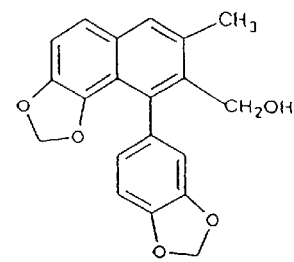
Figure 1B:
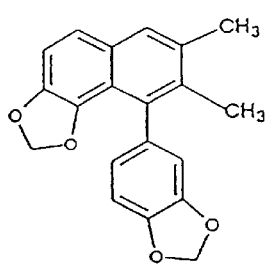
Figure 1B:
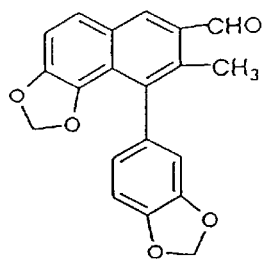
Figure 1B:
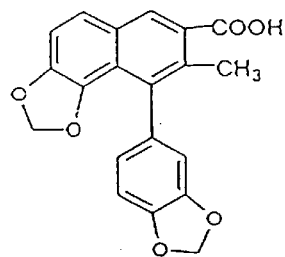
Figure 1B:
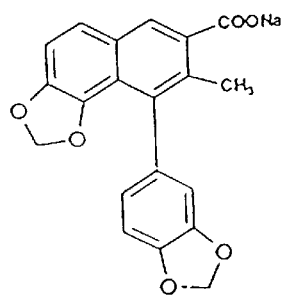
Figure 1C:
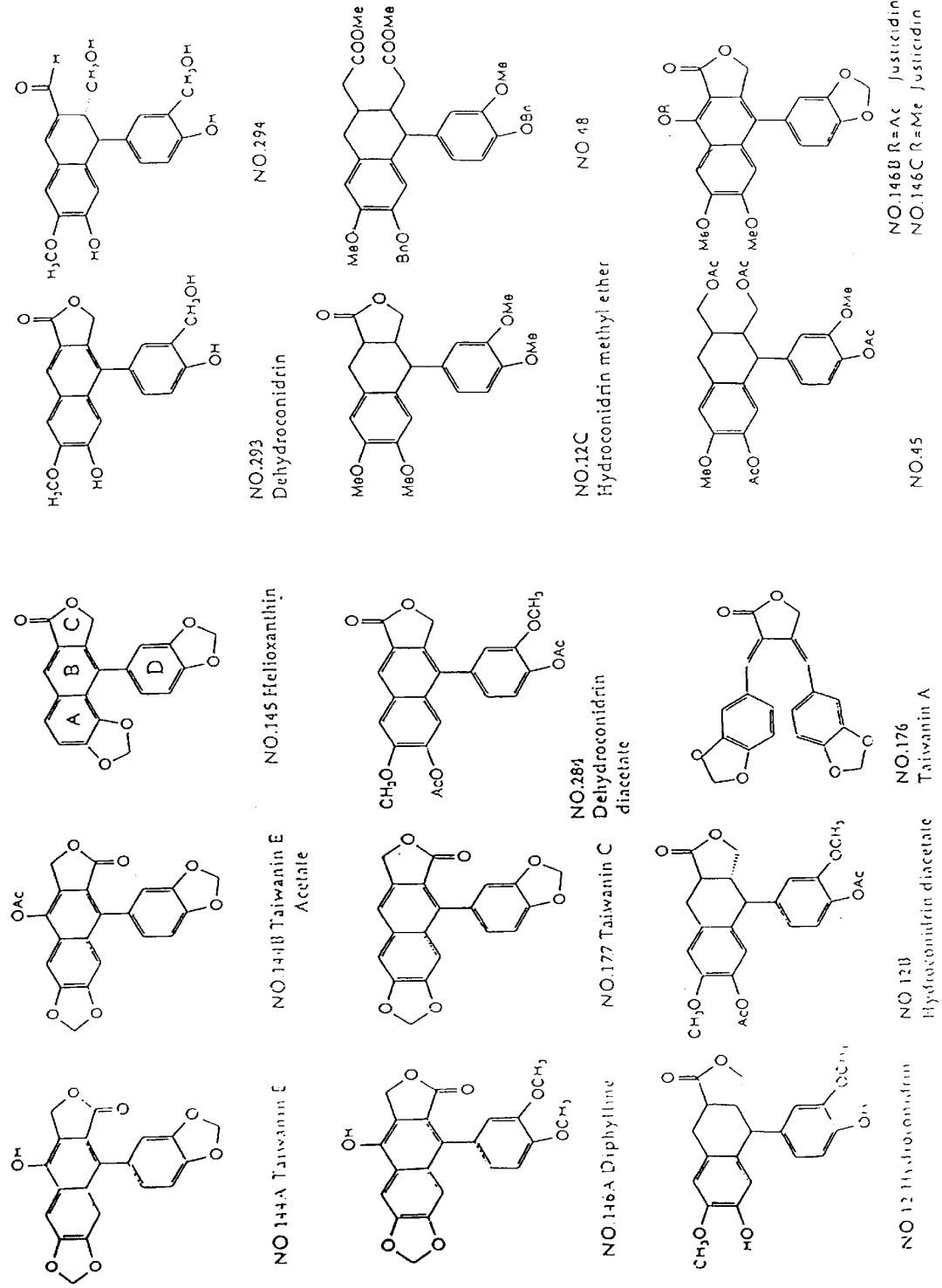
Figure 2A:
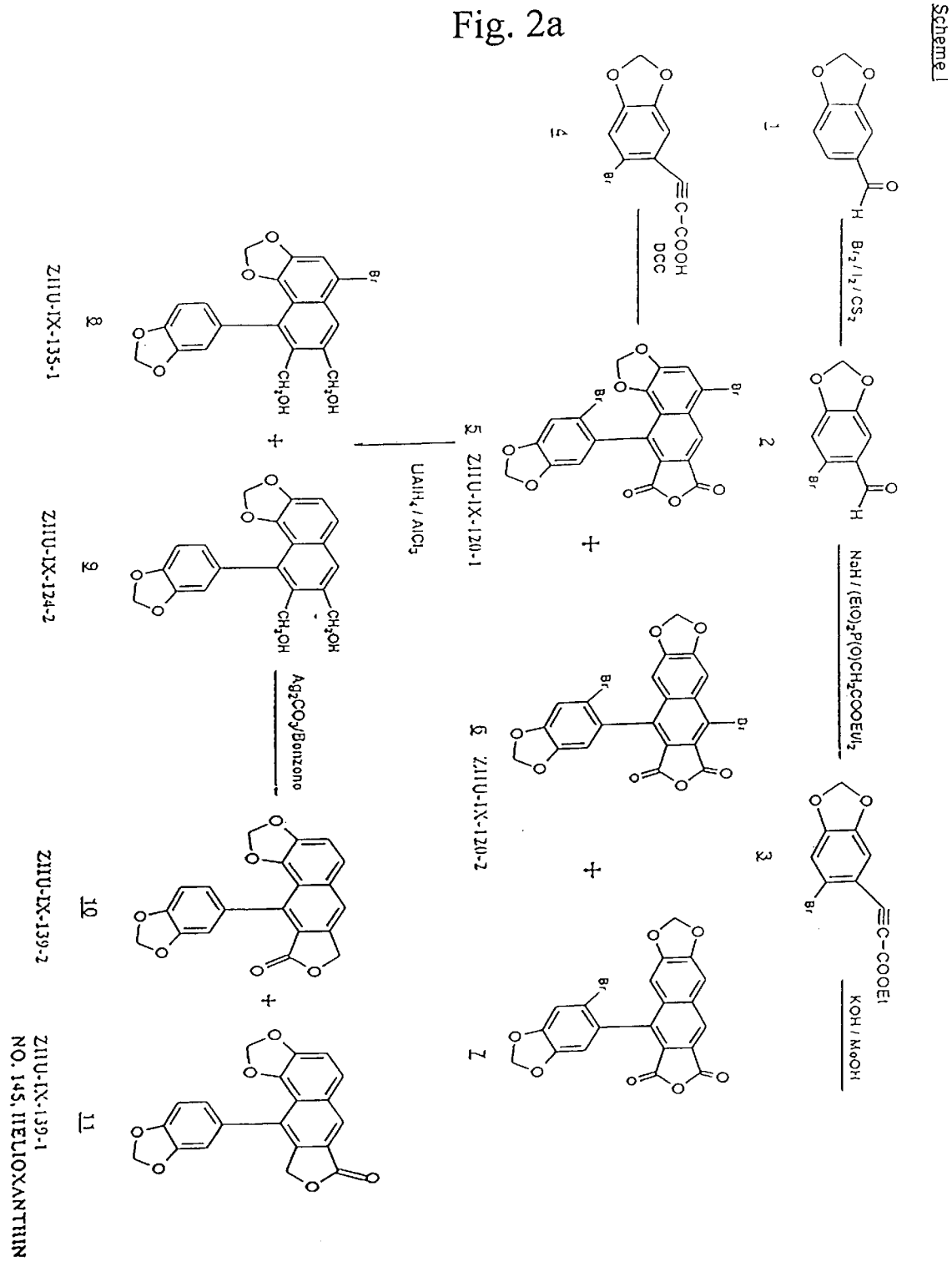
FIGS. 2A and 2B represent the chemical scheme for the synthesis of compounds according to the present invention.
Figure 2B:
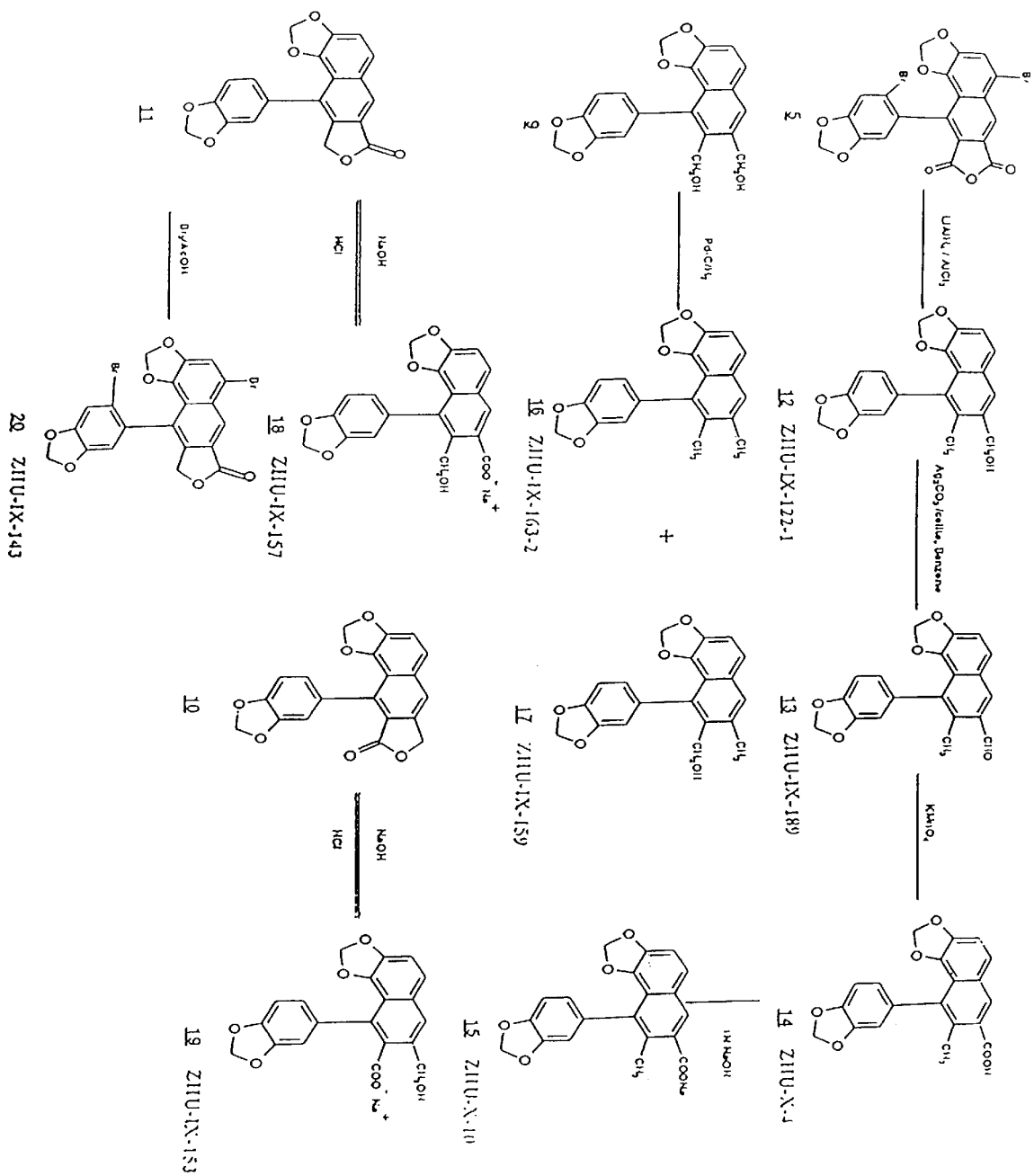

The present invention relates to the discovery that helioxanthin and its analogs, depicted in FIGS. 1A, B and C hereof, exhibit activity against Hepatitis B virus (HBV), Hepatitis C virus (HCV), Yellow Fever virus, Dengue Virus, Japanese Encephalitis, West Nile virus and related flaviviruses. The activity the present compounds display against these viruses is unexpected, given the paucity of research on the activity of these agents in the prior art. The present compounds also unexpectedly exhibit exceptional anti-HBV activity against 3TC (L(-)SddC) resistant HBV.

The present invention relates to compounds according to the structure:

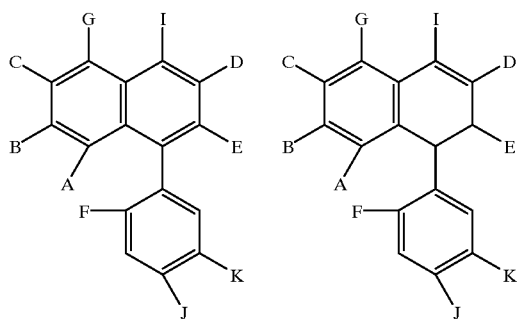

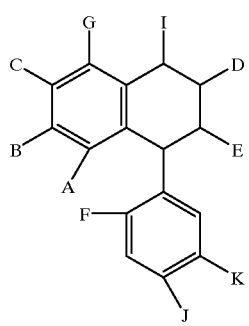

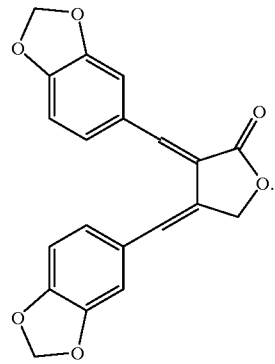

where A is H, OH, OR or forms a 1,3 dioxolane group with B such that A and B are O and are bridged together by a —$CH_2$-(methylene) group;

C is H, OH, OR or forms a 1,3 dioxolane group with B such that B and C are O and are bridged together by a —$CH_2$-(methylene) group;

B is OH, OR or forms a 1,3 dioxolane group with either A or C;

R is a $C_1$ to $C_3$ alkyl or a benzyl group or a $C_1$ to $C_{20}$ acyl group, preferably a $C_1$ to $C_7$ acyl group;

D and E are the same or different and are selected from $CH_3$, $CH_2OH$, $CH_2OR$, CHO, COOH, $COO^-Na^+$, $CH_2COOR^1$ or a keto (C=O) group or —$CH_2$-(methylene) group, with the proviso that when D or E is a keto group, the other of D or E is a keto group or a methylene group and D and E are linked together by an —O— group to form a five-membered lactone ring or a dicarboxylic acid anhydride ring;

$R^1$ is a $C_1$ to $C_3$ alkyl group;

F and G are H or Br;

I is H, OH, OR or Br and

J and K are the same or different and are selected from $CH_3$, $CH_2OH$, $CH_2OR$, CHO, COOH, $COO^-Na^+$ or together form a 1,3 dioxolane ring such that J and K are O and are bridged together by a —$CH_2$-(methylene) group.

The present invention also relates to a compound according to the structure:

The present invention relates to the discovery that helioxanthin and its analogs exhibit activity as agents to inhibit the growth, replication and/or elaboration of Hepatitis B virus (HBV), Hepatitis C virus (HCV), Yellow Fever virus, Dengue Virus, Japanese Encephalitis, West Nile virus and related flaviviruses. Compounds according to the present invention exhibit primary utility as agents for inhibiting the growth or replication of flaviviruses. Certain of these agents are also useful for inhibiting the growth or replication of other viruses (for example, HSV by helioxanthin, among others) or for treating other viral infections and/or related disease states. Other agents may be used as biological probes for testing purposes or as intermediates in the synthesis of related nucleoside compounds having pharmacological activity or for treating cancer and other disease states.

Compounds of the present invention find particular use in combating viral infections which afflict animals, and in particular, humans suffering from Hepatitis B virus (HBV), Hepatitis C virus (HCV), Yellow Fever virus, Dengue virus, Japanese Encephalitis, West Nile virus and related flaviviruses and their complications, especially hepatoma which may be a secondary disease state precipitated by HBV or HCV infections. Compounds according to the present invention offer great potential as therapeutic agents against certain disease states for which there presently are few, if any, real therapeutic options. The compounds according to the present invention may be used alone or in combination with other anti-HBV or anti-flavivirus agents or other therapeutic treatments.

The compounds according to the present invention are based on the natural product helixoxanthin, which may be isolated from the plant of *Taiwania cryptomerioides* and related serial analogs. In a cell culture model, it was determined that helioxanthin selectively inhibited HBV replication and decreased the RNA level. Serial analogs wer designed and synthesized and presented in the examples section of the present specification. The anti-viral activty, cytotoxicty and solubility of the compounds is summarized in Table 1. Interestingly, despite significant activity against HBV and Yellow Fever virus (YFV), the compounds exhibited relatively low toxicity. This is an unexpected result.

The present invention also relates to methods for inhibiting the growth or replication of Hepatitis B virus (HBV), Hepatitis C virus (HCV), Yellow Fever virus, Dengue virus, Japanese Encephalitis, West Nile virus and related flaviviruses comprising exposing the virus to an inhibitory effective amount or concentration of at least one of the disclosed helioxanthin analogs. This method may be used in comparison tests such as assays for determining the activities of related anti-viral compounds as well for determining the susceptibility of a patient's infection to one of the compounds according to the present invention. The present compounds may be used to treat a number of viruses as explained, but the compounds are particularly suited for the treatment of HBV infections which are 3TC resistant.

The therapeutic aspect according to the present invention relates to methods for treating or preventing Hepatitis B virus (HBV), Hepatitis C virus (HCV), Yellow Fever virus, Dengue virus, Japanese Encephalitis, West Nile virus and related flavivirus infections in patients, preferably, human patients, comprising administering anti-viral effective amounts of one or more of the compounds according to the present invention to inhibit the growth or replication of the virus in the animal or human patient being treated. In a preferred method aspect according to the present invention, the present compositions are used to prevent or delay the onset of Hepatitis B virus (HBV), Hepatitis C virus (HCV), Yellow Fever virus, Dengue Virus, Japanese Encephalitis, West Nile virus and related flavivirus infections or related conditions or viral complications in a patient, espcially hepatoma, which may become a disease state secondary to a HBV or HCV infection.

Pharmaceutical compositions based upon these novel chemical compounds comprise one or more of the above-described compounds in a therapeutically effective amount for treating a viral infection, in particular, a Hepatitis B virus (HBV), Hepatitis C virus (HCV), Yellow Fever virus, Dengue Virus, Japanese Encephalitis, West Nile virus and related flavivirus infections. Optionally, pharmaceutical compositions according to the present invention include one or more pharmaceutically acceptable additive, carrier or excipient.

The compounds according to the present invention, in pharmaceutical dosage form, also may be used as prophylactic agents for inhibiting the growth or replication of a virus such as HBV or a flavivirus such as Hepatitis C virus (HCV), Yellow Fever virus, Dengue Virus, Japanese Encephalitis, West Nile virus and related flaviviruses. In certain pharmaceutical dosage forms, the pro-drug form, for example, an acylated version of one of more of the analogs containing a hydroxyl side chain may be preferred.

While not being limited by way of theory, it is believed that the compounds according to the present invention may induce their inhibitory effect on the growth or replication of the virus by virtue of their ability to decrease or inhibt the synthesis of viral RNA, which leads to a decrease in viral RNA, the expression of the viral gene, a decrease in antigen expression and viral replication.

The compounds according to the present invention are produced by synthetic methods which are readily known to those of ordinary skill in the art and include various chemical synthetic methods which are presented in detail hereinbelow.

DETAILED DESCRIPTION OF THE INVENTION

The following definitions will be used throughout the specification to describe the present invention.

The term "patient" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "Hepatitis B Virus" (HBV) is used to describe the virus (serum hepatitis virus) which produces viral heptatis type B in humans. This is a viral disease with a long incubation period (about 50 to 160 days) in contrast to Hepatitis A virus (infectious hepatitis viurs) which has a short incubation period. The virus is usually tramsmitted by injection of infected blood or blood derivatives or mrely by use of contaminated needles, lancets or other instruments. Clinically and pathologically, the disease is similar to viral hepatitis type A; however, there is no cross-protective immunity. Viral antigen (HBAg) is found in the serum after infection.

The term "Hepatitis C Virus" or (HCV) is used throughout the specification to describe the hepatitis virus which is the causative agent of non-A, non-B hepatitis. The Disease in the acute stage is, in general, milder than hepatitis B, but a greater proportion of such infections become chronic.

The term "flavivirus" is used throughout the specification to describe viruses belonging to the genus Flavivirus of the family Togaviridae. According to virus taxonomy, about 50 viruses including Hepatitis C virus (HCV), Yellow Fever virus, Dengue Virus, Japanese Encephalitis virus, West Nile virus and related flaviviruses are members of this genus. The viruses belonging to the genus Flavivirus are simply called flaviviruses. These viruses were formerly classified as group B arboviruses. The flaviviruses are agents of infectious disease and predominate in East, Southeast and South Asia and Africa, although they may be found in other parts of the world as well.

The term "Yellow Fever virus" is used to describe the flavivirus which is the causative agent of yellow fever. Yellow fever is a tropical mosquito-borne viral heptatitis, due to Yellow Fever virus (YFV), with an urban form transmitted by *Aedes aegypti,* and a rural, jungle or sylvatic form from tree-dwelling mammals by various mosquitos of the Haemagogus species complex. Yellow fever is characterized clinically by fever, slow pulse, albuminuria, jaundice, congesion of the face and hemorrhages, especially hematemesis ("black vomit"). It is fatal in about 5–10% of the cases.

The term "Japanese encephalitis virus" ("JEV") is used to describe the flavivirus which is the causative agent of Japanese encephalitis (JE). JE is an epidemic encephalitis or encephalomyelitis of Japan, Russia (Siberia) and other partis of Asia. The mortality rate from JE is rather high and the disease brings heavy sequelae. Although found in Japan, the disease has spread to other parts of Asia and is now found predominantly outside of Japan, primarily in South and Southeast Asia.

The term "Dengue virus" is used throughout the specification to descibe the flavivirus which is the causative agent(s) of dengue fever/dengue hemorrhagic fever. Dengue is a disease of tropical and subtropical regions occurring epidemically and caused by Dengue virus, one of a group of arboviruses which causes the hemorrhagic fever syndrome. Four grades of severity are recognized: grade I: fever and constitutional symptoms, grade II: grade I plus spontaneous bleeding (of skin, gums or gastrointestinal tract), grade III: grade II plus agitation and circulatory failure and grade IV: profound shock. The disease is transmitted by a mosquito of the genus Aedes (generally *A. aegyptiI,* but frequently, *A. albopictus*). Also called Aden, bouquet, breakbone, dandy, date, dengue (hemorrhagic) or polka, solar fever, stiffneck fever, scarlatina rheumatica or exanthesis arthorosia. "Hemorrhagic dengue" is a more pathogenic epidemic form of dengue which has erupted in a number of epidemic outbreaks in the Pacific region in recent years.

The term "West Nile virus" is used to describe the flavivirus which is the causative agent of West Nile fever, a disease characterized by headache, fever, masculopapular rash, myalgia, lymphadenopathy and leukopenia. The virus is spread by Culex mosquitoes from a reservoir in birds.

The term "pharmaceutically acceptable salt" is used throughout the specification to describe a salt form of helioxanthin or one or more of its serial analogs described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids.

The term "pharmaceutically acceptable derivative" is used throughout the specification to describe any pharmaceutically acceptable prodrug form (such as an ester or other prodrug group) which, upon administration to a patient, provides directly or indirectly the present compound or an active metabolite of the present compound.

The term "acyl" is used throughout the specification to describe a group at the 5' position of the nucleoside analog (i.e., at the free hydroxyl position in the dioxolanyl moiety) which contains a $C_1$ to $C_{20}$ linear, branched, aromatic or cyclic alkyl (e.g., cyclopentyl, cyclohexyl) chain. The acyl group on various positions of the present compounds, in combination with the hydroxyl group to which is is generally bound, results in an ester, which, after administration, may be cleaved to produce the free hydroxyl group. Acyl groups according to the present invention are represented by the structure:

where R is a $C_1$ to $C_{20}$ linear, branched, aromatic or cyclic alkyl chain, alkoxyalkyl, aryloxyalkyl, such as phenoxymethyl, aryl, alkoxy, among others. Preferred acyl groups are those where R is $C_1$ to $C_7$. Acyl groups according to the present invention also include, for example, those acyl groups derived from benzoic acid and related acids, 3-chlorobenzoic acid, succinic, capric and caproic, lauric, myristic, palmitic, stearic and oleic, among numerous others including mesylate groups. One of ordinary skill in the art will recognize the acyl groups which will have utility in the present invention, either to synthesize the target pharmaceutical compounds or as prodrug of the nucleosides according to the present invention.

The term "inhibitory effective concentration" or "inhibitory effective amount" is used throughout the specification to describe concentrations or amounts of compounds according to the present invention which substantially or significantly inhibit the growth or replication of susceptible viruses, especially including Hepatitis B virus (HBV), Hepatitis C virus (HCV), Yellow Fever virus, Dengue Virus, Japanese Encephalitis, West Nile virus and related flaviviruses.

The term "therapeutic effective amount" or "therapeutically effective amount" is used throughout the specification to describe concentrations or amounts of compounds according to the present invention which are therapeutically effective in treating Hepatitis B virus (HBV), Hepatitis C virus (HCV), Yellow Fever virus, Dengue Virus, Japanese Encephalitis, West Nile virus and related flavivirus infections in patients.

The term "preventing effective amount" is used throughout the specification to describe concentrations or amounts of compounds according to the present invention which are prophylactically effective in preventing or delaying the onset of Hepatitis B virus (HBV), Hepatitis C virus (HCV), Yellow Fever virus, Dengue Virus, Japanese Encephalitis, West Nile virus and related flavivirus infections or related conditions (especially heptatitis-associated hepatoma) in humans.

The term "effective amount" shall mean an amount or concentration of a compound according to the present invention which is effective within the context of its administration.

The term "pure" is used to describe a compound according to the present invention which has been isolated and is not found in its natural state. Pure compounds according to the present invention are those which preferably comprise at least 95% by weight of the desired compound, more preferably at least about 97–98% by weight of the desired compound and even more preferably about 99+% by weight of the desired compound. Pure compounds according to the present invention, in particular, helioxanthin, are distinguished from compounds which may be found in their natural state, for example, as the metabolic products of biosynthesis by living organisms. Pure compounds include those natural products which have been isolated from a plant or other organism and are in a form which is used to deliver active compound for the treatment of a virus.

The term "enantionmerically enriched" is used throughout the specification to describe a compound which includes at least about 95%, preferably at least about 96%, more preferably at least about 97%, even more preferably, at least about 98%, and even more preferably at least about 99% or more of a single enantiomer of the described compound. Where the enatiomeric enrichment of a compound is unstated, it is presumed (unless the chemistry dictates otherwise) that the compound is a racemic mixture.

The present invention, therefore relates to a group of compounds according to the structure:

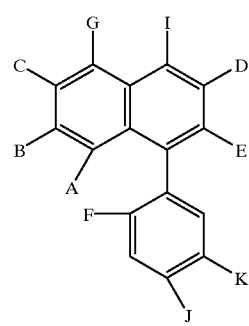

I

-continued

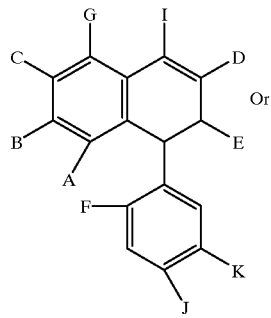

II

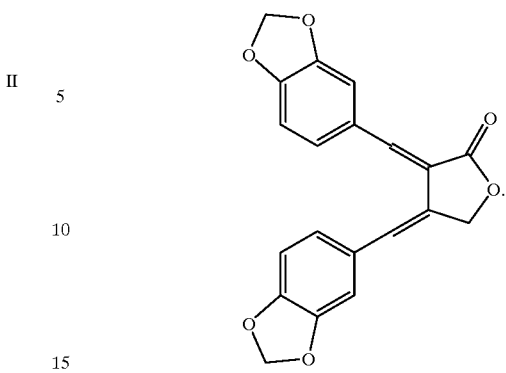

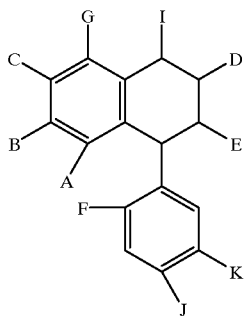

III where A is H, OH, OR or forms a 1,3 dioxolane group with B such that A and B are O and are bridged together by a —$CH_2$-(methylene) group;

C is H, OH, OR or forms a 1,3 dioxolane group with B such that B and C are O and are bridged together by a —$CH_2$-(methylene) group;

B is OH, OR or forms a 1,3 dioxolane group with either A or C;

R is a $C_1$ to $C_3$ alkyl group, a benzyl group or a $C_1$ to $C_{20}$ acyl group, preferably a $C_1$ to $C_7$ acyl group;

D and E are the same or different and are selected from $CH_3$, $CH_2OH$, $CH_2OR$, CHO, COOH, $COO^-Na^+$, $CH_2COOR^1$ or a keto (C=O) group or —$CH_2$-(methylene) group, with the proviso that when D or E is a keto group, the other of D or E is a keto group or a methylene group and D and E are linked together by an —O—group to form a five-membered lactone ring or a dicarboxylic acid anhydride ring;

$R^1$ is a $C_1$ to $C_3$ alkyl group

F and G are H or Br;

I is H, OH, OR or Br and

J and K are the same or different and are selected from $CH_3$, $CH_2OH$, $CH_2OR$, CHO, COOH, $COO^-Na^+$ or together form a 1,3 dioxolane group such that J and K are O and are bridged together by a —$CH_2$-(methylene) group.

The present invention also relates to a compound according to the structure:

The present compounds exhibit unexpectedly high activity against Hepatitis B virus (HBV), Hepatitis C virus (HCV), Yellow Fever virus, Dengue Virus, Japanese Encephalitis, West Nile virus and related flaviviruses. In particular, the compounds according to the present invention show potent inhibition of the replication of the virus (viral growth) in combination with very low toxicity to the host cells (i.e., animal or human tissue).

Compounds according to the present invention exhibit primary utility as agents for inhibiting the growth or replication of Hepatitis B virus (HBV), Hepatitis C virus (HCV), Yellow Fever virus, Dengue Virus, Japanese Encephalitis, West Nile virus and related flaviviruses. Certain of these agents (in particular, helioxanthin) are also useful for inhibiting the growth or replication of other viruses (for example, HSV) or for treating other viral infections and/or related disease states. Other agents may be used as biological probes for testing purposes or as intermediates in the synthesis of related nucleoside compounds having pharmacological activity or for treating cancer and other disease states.

Compounds of the present invention find particular use in combating viral infections which afflict animals, and in particular, humans suffering from Hepatitis B virus (HBV), Hepatitis C virus (HCV), Yellow Fever virus, Dengue Virus, Japanese Encephalitis, West Nile virus and related flavivirus infections and their complications. Compounds according to the present invention offer great potential as therapeutic agents against a number of disease states for which there presently are few real therapeutic options. The present invention find particular use to treat HBV infections which are 3TC (lamivudine) resistant. The compounds according to the present invention may be used alone or in combination with agents or other therapeutic treatments.

The present invention also relates to methods for inhibiting the growth or replication of Hepatitis B virus (HBV), Hepatitis C virus (HCV), Yellow Fever virus, Dengue Virus, Japanese Encephalitis, West Nile virus and related flavivirus comprising exposing the virus to an inhibitory effective amount or concentration of at least one of the disclosed nucleoside analogs. This method may be used in comparison tests such as assays for determining the activities of related anti-viral compounds as well for determining the susceptibility of a patient's viral infection to one of the compounds according to the present invention. The present compounds are preferably used to treat or prevent 3TC-resistant HBV infections and HCV infections in humans.

The therapeutic aspect according to the present invention relates to methods for treating or preventing Hepatitis B virus (HBV), Hepatitis C virus (HCV), Yellow Fever virus, Dengue Virus, Japanese Encephalitis, West Nile virus and related flavivirus infections in patients, preferably, human patients, comprising administering anti-viral effective amounts of one or more of the compounds according to the present invention to inhibit the growth or replication of the virus in the animal or human patient being treated. In a preferred method aspect according to the present invention, the present compositions are used to prevent or delay the onset of Hepatitis B virus (HBV), Hepatitis C virus (HCV), Yellow Fever virus, Dengue Virus, Japanese Encephalitis, West Nile virus and related flavivirus infections or related conditions or viral complications in a patient, especially including hepatoma in those patients who have been infected with HBV or HCV.

Pharmaceutical compositions based upon these novel chemical compounds comprise one or more of the above-described compounds in a therapeutically effective amount for treating a viral, generally, a Hepatitis B virus (HBV), Hepatitis C virus (HCV), Yellow Fever virus, Dengue Virus, Japanese Encephalitis, West Nile virus and related flavivirus infection, optionally in combination with a pharmaceutically acceptable additive, carrier or excipient.

The compounds according to the present invention, in pharmaceutical dosage form, also may be used as prophylactic agents for inhibiting the growth or replication of Hepatitis B virus (HBV), Hepatitis C virus (HCV), Yellow Fever virus, Dengue Virus, Japanese Encephalitis, West Nile virus and related flavivirus. These may be particularly appropriate as anti-viral agents. In certain pharmaceutical dosage forms, the pro-drug form, for example, an acylated form of the compound to promote dissolution, absorptivity or bioavailability may be preferred.

While not being limited by way of theory, it is believed that compounds according to the present invention exhibit their anti-viral activity by virtue of their ability to decrease viral RNA, which leads to a decrease in viral RNA, the expression of the viral gene, a decrease in antigen expression and viral replication. It is unexpected that the present compounds evidence exceptional activity against Hepatitis B virus (HBV), Hepatitis C virus (HCV), Yellow Fever virus, Dengue Virus, Japanese Encephalitis, West Nile virus and related flaviviruses. The present compounds also exhibit unexpected activity against 3TC resistant HBV.

The use of helioxanthin in cell cultures has shown a stronger inhibition of viral replication of strains of HBV that have become resistant to 3TC. Furthermore, the helioxanthin compounds have a unique mechanism of anti-viral action. It is believed that helioxanthin No. 145, is the only compound that could simultaneously decrease the RNA level of HBV and its antigen expression as well as inhibit HBV replication in cell culture. In contrast to other nucleotide analogs which only inhibit HBV during viral DNA synthesis, helioxanthin compounds according to the present invention inhibit the virus at an early stage of the viral cycle in which HBV replicates via reverse transcription of a 3.5 kb pregenomic RNA as well as viral gene expression in virus DNA expression cells.

As stated earlier, the Helioxanthin compounds could preferentially decrease viral RNA in cells; therefore, viral gene expression and replication could also decrease. The unique anti-viral action of the has never been found in drugs that have been used or evaluated in clinical trials. The critical site of the structure in helioxanthin that is responsible for anti-viral activity has recently been elucidated.

The helioxanthin compounds according to the present invention can be used alone or in combination with other drugs for the treatment of HBV infection, or an infection of flavivirus including Yellow fever virus, Hepatitis C virus, Danque fever virus, Japanese Encephalitis virus, West Nile virus as well as the prevention of diseases associated with these viruses including hepatoma.

The present compounds are preferably used in pharmaceutical dosage form. In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether derivatives and various pharmaceutically acceptable salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, in preferred embodiments, a Hepatitis B virus (HBV), Hepatitis C virus (HCV), Yellow Fever virus, Dengue Virus, Japanese Encephalitis, West Nile virus and related flavivirus infection. In general, a therapeutically effective amount of the present compound in pharmaceutical dosage form usually ranges from about 0.1 mg/kg to about 100 mg/kg or more, more preferably, slightly less than about 1 mg./kg. to about 50 mg./kg. of the patient or considerably more, depending upon the compound used, the condition or infection treated and the route of administration. In the case of HBV or HCV infections, the active compound is preferably administered in amounts ranging from about 0.5 mg/kg to about 25 mg/kg of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compounds or their pharmaceutically acceptable salts thereof can also be mixed with other active materials that do not impair the desired action, or with materials that supplement the desired action, such as other antivirals, or depending upon the desired target or therapy, antibiotics, antifungals, antinflammatories.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of admnistration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prod-drug forms of the nucleoside compounds according to the present invention.

In particularly preferred embodiments according to the present invention, the compounds and compositions are used to treat, prevent or delay the onset of viral infections of mammals and in particular, Hepatitis B virus (HBV), Hepatitis C virus (HCV), Yellow Fever virus, Dengue Virus, Japanese Encephalitis, West Nile virus and related flavivirus infections in humans. In its preferred embodiments, the compounds are used to treat HBV, and HCV infections, especially 3TC resistant HBV infections in humans. Preferably, to treat, prevent or delay the onset of virus infections pursuant to the present invention, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form.

The compounds according to the present invention, because of their low toxicity to host cells, may advantageously be employed prophylactically to prevent Hepatitis B virus (HBV), Hepatitis C virus (HCV), Yellow Fever virus, Dengue Virus, Japanese Encephalitis, West Nile virus and related flavivirus infection infections or to prevent the occurrence of clinical symptoms associated with the viral infection, especially hepatoma in those patients with HBV or HCV viral infections. Thus, the present invention also encompasses methods for the prophylactic treatment of viral infections, and in particular Hepatitis B virus (HBV), Hepatitis C virus (HCV), Yellow Fever virus, Dengue Virus, Japanese Encephalitis, West Nile virus and related flavivirus infection infections. In this aspect according to the present invention, the present compositions are used to prevent or delay the onset of an Hepatitis B virus (HBV), Hepatitis C virus (HCV), Yellow Fever virus, Dengue Virus, Japanese Encephalitis, West Nile virus and related flavivirus infection or a related disease such as hepatoma in patients, among others. This prophylactic method comprises administering to a patient in need of such treatment or who is at risk for the development of a Hepatitis B virus (HBV), Hepatitis C virus (HCV), Yellow Fever virus, Dengue Virus, Japanese Encephalitis, West Nile virus and related flavivirus infection or related symptoms or diseases an amount of a compound according to the present invention effective for alleviating, preventing or delaying the onset of the the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of the present compounds, these may be administered within the same dosage range for therapeutic treatment (i.e., about 250 micrograms up to about 500 mg. or more from one to four times per day for an oral dosage form) as a prophylactic agent to prevent the proliferation of a virus infection, or to prolong the onset of a virus infection which manifests itself in clinical symptoms.

In addition, compounds according to the present invention may be administered alone or in combination with other agents, including other compounds of the present invention.

Certain compounds according to the present invention may be effective for enhancing the biological activity of certain agents according to the present invention by reducing the metabolism, catabolism or inactivation of other compounds and as such, are co-administered for this intended effect.

In a particularly preferred pharmaceutical composition and method for treating HBV, HCV or a 3TC-resistant HBV infection, an inhibitory effective amount of at least one compound according to the present invention in pharmaceutical dosage form is administered to a patient suffering from such an infection to treat the infection and alleviate the symptoms of such infection.

As indicated, compounds according to the present invention may be administered alone or in combination with other agents, especially including other compounds of the present invention or compounds which are otherwise disclosed as being useful for the treatment of Hepatitis B virus (HBV), Hepatitis C virus (HCV), Yellow Fever virus, Dengue Virus, Japanese Encephalitis, West Nile virus and related flavivirus infection, such as those relevant compounds and compositions which are disclosed in the following United States patents, which are incorporated by reference herein: U.S. Pat. Nos. 5,922,757; 5,830,894; 5,821,242; 5,610,054; 5,532,215; 5,491,135; 5,179,084; 4,902,720; 4,898,888; 4,880,784; 5,929,038; 5,922,857; 5,914,400; 5,922,711; 5,922,694; 5,916,589; 5,912,356; 5,912,265; 5,905,070; 5,892,060; 5,892,052; 5,892,025; 5,883,116; 5,883,113; 5,883,098; 5,880,141; 5,880,106; 5,876,984; 5,874,413; 5,869,522; 5,863,921; 5,863,918; 5,863,905; 5,861,403; 5,852,027; 5,849,800; 5,849,696; 5,847,172; 5,627,160; 5,561,120; 5,631,239; 5,830,898; 5,827,727; 5,830,881 and 5,837,871, among others. The compounds disclosed in the above-referenced patents may be used in combination with the present compounds for their additive activity or treatment profile against Hepatitis B virus (HBV), Hepatitis C virus (HCV), Yellow Fever virus, Dengue Virus, Japanese Encephalitis, West Nile virus and related flavivirus infections and, in certain instances, for their synergistic effects in combination with compounds of the present invention. Preferred secondary or additional compounds for use with the present compounds are those which do not inhibit Hepatitis B virus (HBV), Hepatitis C virus (HCV), Yellow Fever virus, Dengue Virus, Japanese Encephalitis, West Nile virus and related flavivirus infection by the same mechanism as those of the present invention.

The compounds according to the present invention are produced by synthetic methods which are readily known to those of ordinary skill in the art and include various chemical synthetic methods which are presented in detail hereinbelow.

During chemical synthesis of the various compositions according to the present invention, one of ordinary skill in the art will be able to practice the present invention without engaging in undue experimentation. In particular, one of ordinary skill in the art will recognize the various steps that should be performed to introduce a particular substituent at the desired position of the napthalene group or benzene ring, following the specific teachings of the present invention and well-know principles of aromatic chemistry. These steps are well-known in the art. In addition, chemical steps which are taken to "protect" functional groups such as hydroxyl or amino groups, among others, as well as "de-protect" these same functional groups, will be recognized as appropriate within the circumstances of the syntheses. A large number of protecting groups may be used in the present invention. In the case of the introduction of any one or more acyl groups onto a hydroxyl group, standard techniques, well known by those of ordinary skill, may be used. Synthesis of other prodrug forms of the present compounds may also be synthesized by well-known methods in the art.

Synthesis of Arylnapthalene Lignans Derivatives

Compound (10) was synthesized as depicted in Scheme I. (Synthesis of Dehydrotobain. Brown, D. and Stevenson, R. *J. Org Chem.* (1965) 30: 1759; Arylnapthalene Lignans: synthesis of Helioxanthins. Holmes, T. L. and Stevenson, R. *J.Chem. Soc.* (C), (1971), 2091 and Synthesis of Helioxanthin. Holmes, T. L. and Stevenson, R. *Tetrahedron Letter* (1970), 199).

Bromination of piperonal (1) readily gave 6-bromopiperonal (2) which was conveniently converted to ethyl-2-bromo-4,5-methylenedioxyphenylpropiolate (3) by treatment with triethyl phosophonoiodoacetate under the general conditions devised by Wadsworth and Emmons for the synthesis of propiolate esters. The corresponding 2-bromo-4, 5-methylenedioxyphenylpropiolic acid (4) was obtained by alkaline hydrolysis of the ester (crude). Treatment of compound (4) with dicyclohexylcarbodiimide in DMSO to form the anhydride followed by closure of the ring yielded 5-bromo-7,8-methylenedioxy-1-(2'-bromo-4',5'-methylenedioxyphenyl)napthalene-2,3-dicarboxylic acid anhydride (5), 1-bromo-6,7-methylenedioxy-4-(2'-bromo-4', 5'-methylenedioxyphenyl)napthalene-2,3-dicarboxylic acid anyhdride (6) and 6,7-methylenedioxy-1-(2'-bromo-4',5'-methylenedioxyphenyl)napthalene-2,3-dicarboxylic acid anhydride (7). The conversion of the dibromo-anhydride 5 into 2,3-dihydroxymethyl-5-bromo-7,8-methylenedioxy-1-(3', 4'-methylenedioxyphenyl)napthalene (8) and 2,3-dihydroxymethyl-5,6-methylenedioxy-4-(3',4'-methylenedioxyphenyl)napthalene (9) was accomplished on using lithium aluminum hydride and aluminum chloride in THF. Selective oxidation of compound 9 using silver carbonate -celite reagent yielded 7,8-methylendioxy-1-(3',4'-methylenedioxyphenyl)-3-hydroxymethylnapthalene-2-carboxylic acid lactone (10) and 7,8-methylenedioxy-1-(3', 4'-methylenedioxyphenyl)-2-hydroxymethylnaphthalene-3-carboxylic acid lactone (11).

Compound 11 was treated with bromine to yield 8,2'-dibromo-5,6-methylenedioxy-4-(4',5'-methylenedioxyphenyl)-3-hydroxymethylnapthalene-2-carboxylic acid lactone (20). (Arylnapthalene Lignans: synthesis of Helioxanthins. Holmes, T. L. and Stevenson, R. *J.Chem. Soc.* (C), (1971), 2091) Hydrogenolysis of compound 9 gave 2,3-dimethyl-6,7 methylenedioxy-1-(3',4'-methylenedioxyphenyl)naphthalene (16) and 3-methyl-7,8-methylenedioxy-1-(3',4'-methylenedioxy-1-(3',4'-methylenedioxyphenyl)-2-hydroxymethylnaphthalene (17). (Synthesis of Dehydrotobain. Brown, D. and Stevenson, R. *J. Org Chem.* (1965) 30: 1759)

Compounds 10 and 11 were treated with sodium hydroxide to yield sodium 5,6-methylenedioxy-4-(3',4'-methylenedioxyphenyl)-3-hydroxymethylnapthalene-2-carbonate (18) and sodium 7,8-methylenedioxy-1-(3',4'-methylendioxyphenyl)-3-hydroxymethylnapthalene-2-carbonate (19).

Compound 5 was reduced using lithium aluminium hydride and aluminum chloride (Arylnapthalene Lignans: synthesis of Helioxanthins. Holmes, T. L. and Stevenson, R. *J.Chem. Soc.* (C), 1971, 2091) in THF for three days to give 3-methyl-5,6-methylenedioxy-4-(3',4'-methylenedioxyphenyl)-2-hydroxymethylnapthalene (12). Oxidation of compound 12 using silver carbonate-cellite reagent (Arylnapthalene Lignans: synthesis of Helioxanthins. Holmes, T. L. and Stevenson, R. *J.Chem. Soc.* (C), (1971), 2091 and Synthesis of Helioxanthin. Holmes, T. L. and Stevenson, R. *Tetrahedron Letter* (1970), 199) yielded 5,6-methylenedioxy-4-(3',4'-methylendioxyphenyl)-2-methylnapthalene-3-aldehyde (13), which was further oxidized (Asymmetric Hydroformylation Catalyzed by Homogeneous and Polymer-Supported Platinum Complexes Containing Chiral Phosphine Ligands. Parrinello G. And Stille J. K. *J. Am. Chem Soc.* (1987), 109, 7122) using potassium permanganate to give 5,6-methylenedioxy-4-(3', 4'-methylenedioxyphenyl)-2-methylnapthalene-3-carbolic acid (14). Compound 14 was treated with sodium in the methanol to yield sodium 5,6-methylenedioxy-4-(3',4'-methylenedioxyphenyl)-2-methylnapthalene-3-carbonate (15).

Experimental Section

Compound (10) was synthesized as depicted in Scheme I. Synthesis of 3-Methyl-5,6-methylenedioxy-4-(3',4'-methylendioxyphenyl)-2-hydroxymethylnapthalene (12): 5-Bromo-7,8-methylenedioxyphenyl-1-(2'-bromo-4',5'-methylendioxyphenyl)napthalene-2,3-dicarboxylic acid anhydride (5, 3.0 g, 5.76 mmol) was added to a mixture of lithium alumimum hydride (3.0 g) and aluminum chloride (3.0 g) in tetrahydrofuran (600 mL) and suspension was refluxed for 24 hours. Addition of lithium alumimum hydride (3.0 g) and alumimum chloride (3.0 g) was added and reaction solution was heated under reflux for 48 h. Ethyl acetate (1200 mL) was added into the reaction mixture followed by saturated bicarbonate solution (100 ml). The mixture was filtered and filtrate was distilled under reduced pressure to give a syrup, which was purified by silica gel column (Hexane-Ethyl acetate;5:2) to afford three compounds: 3-methyl-7,8-methylenedioxy-1-(3',4'-methylenedioxyphenyl)-2-hydroxymethylenaphtalene (17) (Synthesis of Dehydrotobain. Brown, D. and Stevenson, R. *J. Org Chem.* (1965) 30: 1759) as a white powder (29 mg, 1.5%):mp 207–209° C.; $^1$HNMR (CDCL$_3$) δ7.62 (s, 1H, 1-H), 7.28 (d, 1H, 7-H), 7.18(d, 1H, 8-H), 7.10 and 6.82 (2s, 3H, 2', 3' and 6'-H), 6.03 (dd, 2H, 5,6-methylenedioxy group), 5.86 (s, 2H, 3',4'-methylenedioxy group), 4.50 (s, 2H, 2-CH$_2$OH), 2.63 (s, 3H, 3-CH$_3$), 1.56 (s, 1H, OH, D$_2$O exchangeable); MS m/e 336 (M$^+$); 3-Methyl-5,6-methylenedioxy-4-(3',4'-methylenedioxyphenyl)-2-hydroxymethylnapthalene (12) as white crystals (672 mg, 35%): mp 108–110° C.; $^1$HNMR (CDCL$_3$) δ7.78(s, 1H, 1-H), 7.40 (d, 1H, 7-H), 7.13 (d, 1H, 8-H), 6.86 (d, 1H, 2'-H), 6.68 (dd, 2H, 5,6-methylenedioxy group),6.03 (s, 2H, 3',4'-methylenedioxy group), 5.78 (s, 2H, 2-CH$_2$OH), 2.16 (s, 3H, 3-CH$_3$), 1.59 (s, 1H, OH, D$_2$O exchangeable); MS m/e 336 (M$^+$); 2,3-dihydroxymethyl-5,6-methylenedioxy-4-(3',4'-methylenedioxy-4-(3',4'-methylenedioxphenyl) napthalene (9) (Arylnapthalene Lignans: synthesis of Helioxanthins. Holmes, T. L. and Stevenson, R. *J. Chem. Soc.* (C), (1971), 2091) as a white powder (620 mg, 32%)

Synthesis of 5,6-methylenedioxy-4-(3',4'-methlenedioxphenyl)-2-methylnapthalene -3- aldehyde (13)

The silver carbonate-cellite reagent (5.26 g) was added to a solution of compound 12 (270 mg, 0.80 mmol) in benzene (400 ml). The solvent was distilled off until the vapour temperature reached 80° C. The mixture was heated under reflux for 2 h. The reaction mixture was filtered and cooled. Removal of solvent yielded a syrup, which was purified by silica gel column (Hexane:Ethyl acetate;4:1) to give the aldehyde compound, as pale yellow crystals (249 mg, 93%): mp 216–217 ° C.; $^1$HNMR(CDCL$_3$) δ10.22 (s, 1H, CHO), 8.48 (s, 1H, 1-H), 7.80 (d, 1H,7-H), 7.39 (d, 1H, 8-H), 6.94, 6.78 and 6.64 (d, d, and dd, 3H, 2', 3' and 6'H), Synthesis of 5,6-methylenedioxy-4-(3', 4'-methylenedioxyphenyl)-2-methyln aphthalene-3-carboxylic acid (14)

Compound 13 (160 mg, 0.48 mL) was dissolved in acetone (50 mL) at 50° C. While stirring, a solution of potassium permangnate (132 mg, 0.83 mmol) in acetone (10 mL) was then added dropwise over 30 min. The reaction mixture was stirred for an additional 4 h nad this procedure was repeated once more. The solvent was removed and solid residue was treated with water (50 mL×3) and filtered. The cold aqueous solution was washed with CH$_2$Cl$_2$, then acidified with hydrochloric acid to ph 2 and extracted with CH$_2$CL$_2$. The organic layer was dried over MgSO$_4$. Removal of the solvent under reduced pressure gave a syrup, which was crystallized from methanol to yield 29 mg of product. The mother liquid was distilled to give a syrup, which was purified by silica gel column (Ethyl acetate: Hexane;2:3) to give a yellowish powder (55 mg; 50%); mp 145–146° C.; $^1$HNMR (d$_6$-DMSO) δ12.9 (s, 1H, COOH), 8.36 (s, 1H, 1-H). 7.69 (d, 1H, 7-H), 7.32 (d, 1H, 8-H), 6.93, 6.78 and 6.64 (d, s, and dd, 3H, 2',3' and 6'-H), 6.04 (d, 2H, 5,6-methylenedioxy group), 5.83 (d, 2H, 3',4'-methylenedioxy group), 2.22 (s, 3H, 3-CH$_3$); MS m/e 350 (M$^+$).

Synthesis of Sodium 5,6-methylenedioxy-4-(3',4'-methylenedioxyphenyl)-2methyl napthalene-3-carbonate (15)

1N Sodium hydroxide (0.18 ml) was added to the solution of compound 14 (41 mg, 0.117 mmol) in THF (15 mL). The mixture was stirred at room tempearature for 4 h. The solvent was removed to give a residue, which was purified by silica gel column (CH$_2$Cl$_2$:CH$_3$OH; 3:1) to give 31 mg (71%) of product: mp 210–212° C.: 1HNMR (d$_6$-DMSO) δ7.81 (s, 1H, 1-H), 7.40 (d, 1H, 7-H), 7.13 (d, 1H, 8-H), 6.87, 6.67 and 6.57 (d, s, and d, 3H, 2',3' and 6'-H), 6.06 (d, 2H, 5,6-methylenedioxy group), 5.72 (d, 2H, 3',4'-methylendioxy group), 2.12 (s, 3H, 3-CH$_3$).

Synthesis of Sodium 5,6-methylenedioxy-4-(3',4'-methylenedioxyphenyl)-3-hydroxymethylenapthalene-2-carbonate (18)

10% Sodium hydroxide (1 mL) was added to the solution of compound 11 (20 mg, 0.057 mmol) in methanol (15 mL). The mixture was stirred at 70° C. for 30 minutes. The solvent was removed to give a crude product, which was purified by silica gel column (CH$_2$Cl$_2$: CH$_3$OH; 3:1) to a white powder (18 mg, 82%); mp 128–130° C. $^1$HNMR (d$_6$-DMSO) δ8.26 (s, 1H, 1-H), 7.57 (d, 1H, 7-H), 7.28 (d, 1H, 8-H), 7.25 and 6.82 (2s, 3H, 2',3'and 6'-H), 6.14 (d, 2H, 5,6-methylenedioxy group), 5.83 (d, 2H, 3',4'-methylenedioxy group), 4.30, 4.04 (2dd, 2H, 3-CH$_2$), 1.22 (s, 1H, OH, D$_2$O exchangeable).

Synthesis of Sodium 7,8-methylenedioxy-1-(3',4'-methylenedioxphenyl)-3-hydroxymethylenapthalene-2-carbonate (19)

The compound was synthesized from 10 (20 mg, 0.057 mmol) by the methodology as described for the synthesis of 18: yield 16 mg (72%) as white crystals; mp (213–215° C.;

$^1$HNMR (d$_6$-DMSO) δ7.73 (s, 1H, 1-H), 7.45 (d, 1H, 7-H), 7.19 (d, 1H, 8-H), 7.08 and 6.79 (2s, 3H 2',3', and 6'-H), 6.06 (d, 2H, 5,6-methylenedioxy group), 5.79 (d, 2H, 3',4'-methylenedioxy group), 4.50 (m, 2H, 3-CH$_2$), 1.22 (s, 1H, OH, D$_2$O exchangeable).

Biological Activity

HBV Activity

Figure 3A:
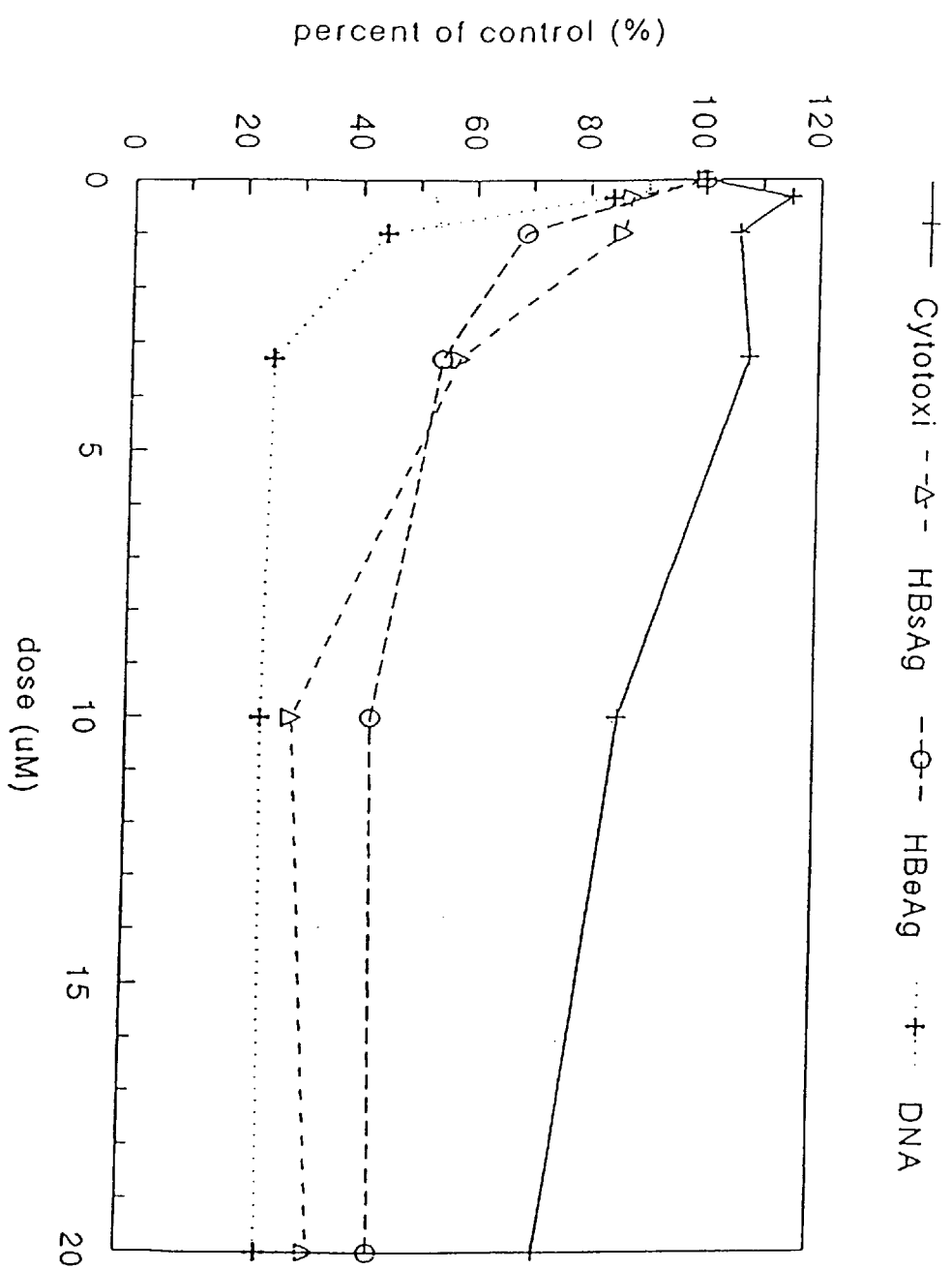
FIGS. 3A and B and 4A, B and C set forth biological data which is presented in the examples section which relates to HBV inhibition by certain compounds according to the present invention.

Helioxanthin and a number of analogs were tested aginast HBV in the following system as follows:

The biological activity of the present compounds was assessed as described by Doong, S-L, et al., *Proc. Natl. Acad. Sci. U.S.A* 88, 8495–8499 (1991). The human hepatoma cell line carrying HBV (cell line designated 2.2.15) provided by Dr. G. Aces was used in the study. Price, et al., *Proc. Natl. Acad. Sci. U.S.A.* 86, 8541 (1989). Briefly, six day-old cultures were treated with varying concentrations of the drug in the culture medium (Minimum essential medium with Earl's salts and 10% fetal bovine serum). The drug was left in the culture medium for a period of 3 days after which period the medium was aspirated and fresh medium containing the same concentration(s) of the drug was added. At the end of the subsequent 3 day period, the culture medium was harvested. The culture medium was processed for obtaining the virions by the polyethylene glycol precipitation method (Doong, et al., supra). Viral DNA thus recovered from the secreted particles was subjected to Southern analysis. Inhibition of the viral replication was determined by the comparison of the viral DNA from drug-treated versus control cultures not treated with the drug. In addition, supernatant obtained from the polyethylene glycol precipitation of the cell culture medium (above) was measured for the presence of two HBV antigens (HBsAg and HBeAg) using enzyme immunoassay kits from Abbott Laboratories, Inc. [HBs (rDNA) EIA and HBe (rDNA)EIA], pursuant to standard practice (FIG. 3A). RNA levels were determed using Northern analysis with cellular albumin RNA being measured as a load control to standardize the quality of the HBV RNA measurement (FIG. 3B).

To determine the cellular toxicity of the present compounds, the T-lymphoblastoic cell line (CEM) and the HEP-G2 cell line (parent cell line from which 2.2.15 cell line is produced) were used. Cells were subjected to varying concentrations of the drug(s) and cell numbers were determined 3 days post treatment by the method described by Chen, C-H and Cheng, Y-C, *J. Biol. Chem.*, 264, 11934 (1989). Concentrations of the drug which would result in inhibition of cell growth were determined from the plot generated by representing cell numbers corresponding to the individual drug concentrations. Results of the cytotoxicity study are set forth in FIG. 3A hereof.

Figure 3B:
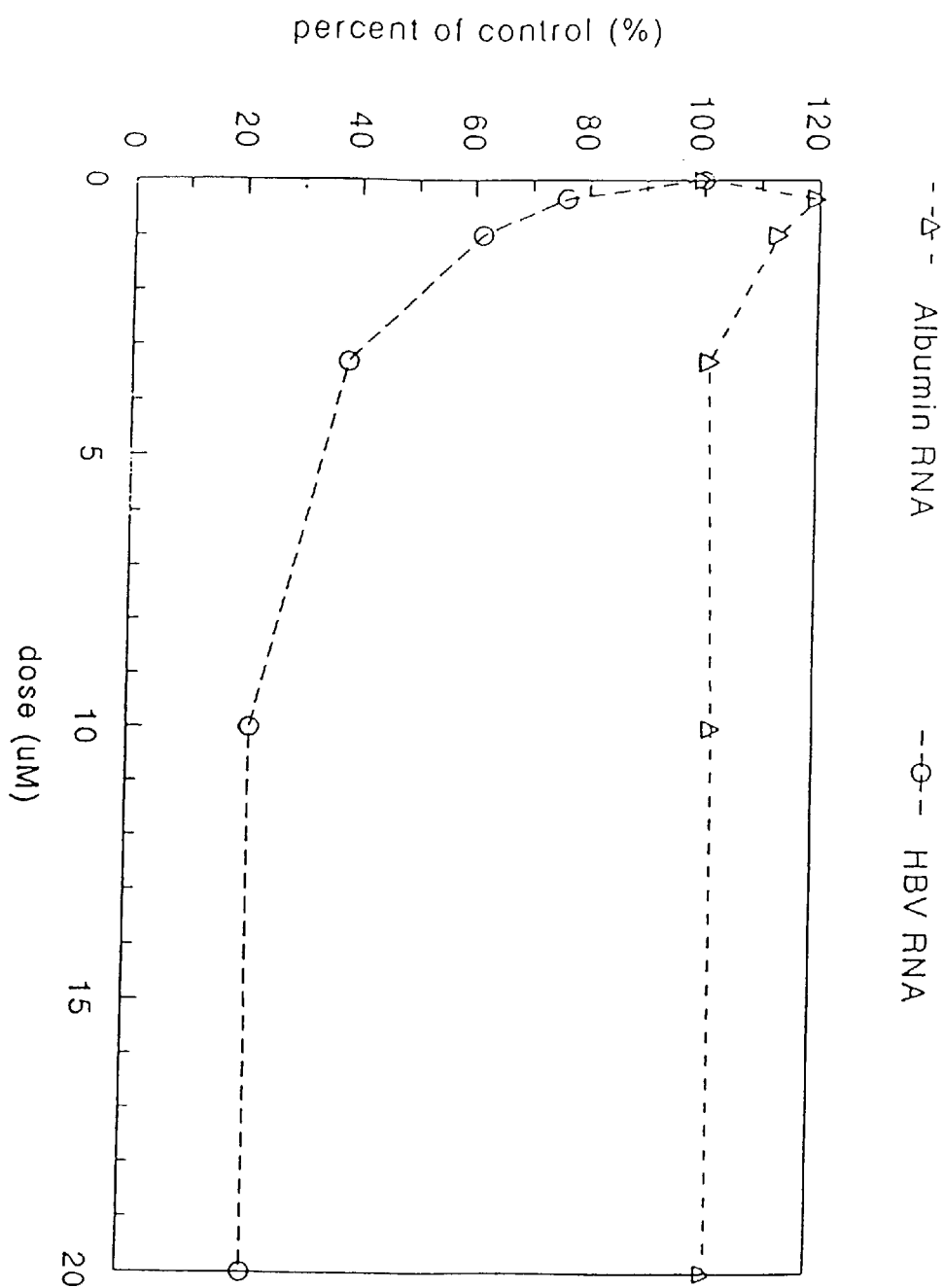

As shown in FIGS. 3A and 3B respectively, compound no. 145 (helioxanthin) selectively inhibited HBV replication, antigen expression and decreased the RNA and DNA level. Serial analogs have been designed and synthesized. FIGS. 1A, B and C and show such compounds. The anti-viral activity, cytotoxicity and solubility of a number of these agents are summarized in Table 1, below. Table 2 further describes the anti-HBV activity of several of these compounds by measurement of the suppression of HBV antigen expression in HepA2 and Hep3B cell lines.

3TC Resistant HBV

In order to test the activity of the present compounds against 3TC resistant HBV, the cell line HepG2 was transfected with plasmids which contained a double mutation which conferred resistance to 3TC following the procedure of Fu and Cheng, *Biochem. Pharm.*, 55, 1567–1572 (1998) and *Biochem. Pharm.*, 57, 1351–1359 (1999). In order to establish a stable HBV producing cell culture system for drug screening against L(-)SddC (3TC), HBV genome constructs were introduced into a retro-viral vector according to that same procedure. These vectors included wild-type (WT) with no mutation for 3TC resistance and L526MM550V (DM) for double mutation evidencing strong 3TC resistance. Each of these retro-viral vectors was transfected into HepG2 cells. Promising cell cultures which secreted HBV antigen (HbsAg and HbeAg) were selected. Among those selected cells, some could secrete HBV virion. The colonies WT10 and DM2 were selected as models to do further characterization studies. A dose response relationship developed for these cell lines indicated that the HBV DNA production of WT10 was sensitive to 3TC (L(-)SddC) and that of DM2 was resistant to 3TC.

Figure 4A:
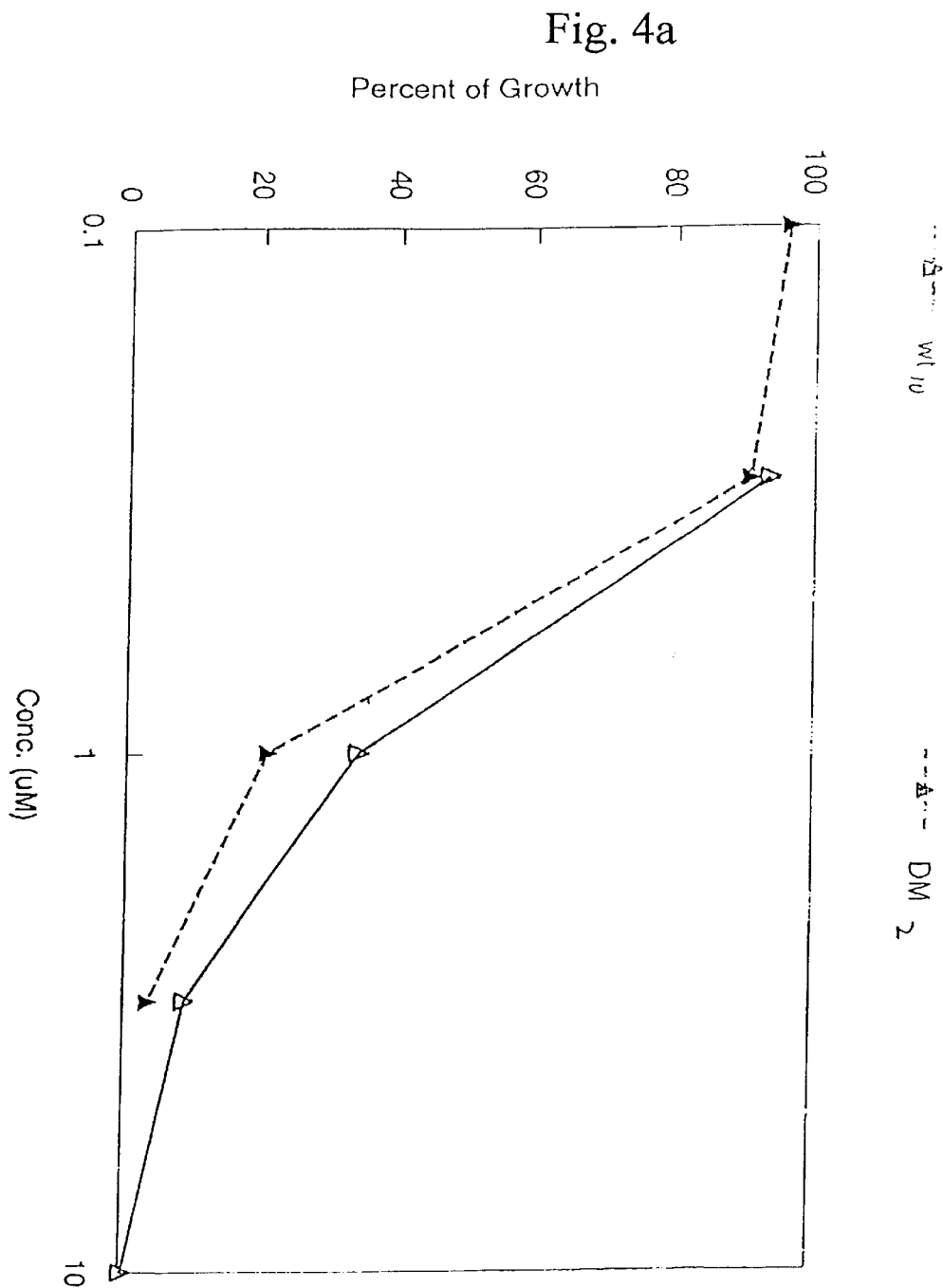

In testing the activity of helioxanthin no. 145, the above-described transient transfected HEPG2 cells were treated with varying concentrations of helioxanthin no. 145 to determine whether helioxanthin had any impact on 3TC resistant HBV. In this study, the transient transfected HepG2 cells (WT and DM2 described above) were treated with an appropriate concentration of helioxanthin when the original calcium phosphate precipitated medium was replaced. Every 3 days, a half volume of fresh medium containing helioxanthin at a certain concentration was added (see FIGS. 4A, 4B and 4C). After 9 days, the cultures were harvested and the HBV progeny were tested for DNA content (Southern analysis). In addition, HBV antigens (HBVe antigen and HBVs antigen) were analyzed using the appropriate ELISA kit from Abbott Laboratories as described above. As evidenced by the data set forth in attached FIGS. 4A, 4B and 4C, helioxanthin had essentially the same effect on 3TC resistant HBV (DM2) as on 3TC sensitive HBV. The data evidences that helioxanthin 145 evidences excellent anti-HBV activity even in 3TC (L(-)SddC) resistant HBV and can be used therapeutically for treatment of 3TC resistant HBV and in combination therapy with 3TC for the treatment of HBV infections.

Activity Against Yellow Fever Virus

Yellow Fever Plaque Reduction Assay

The following procedure was used to test the present compounds against Yellow Fever virus. Baby Hamster Kidney (BHK) cells were seeded onto 24 well dishes at 5×10$^5$ cells per well in RPMI 1640+5% FBS cell medium in 0.1% methyl cellulose (viscosity 15 cps). The cells were incubated overnight in 5% CO$_2$ at 37° C. overnight. The incubated cells were infected with yellow fever at 30 PFU in the presence or absence of drugs (see Table I, below). The infected cells were incubated at 37° C. in 5% CO$_2$ for 30 minutes and overlayed with drugs in RPMI+2% FBS+1% methyl cellulose (viscosity 4,000 cps). The cells in this state were incubated for 6 days at 37° C. in 5% CO$_2$, after which time the cells in each well were stained with 0.8% Crystel Violet. The ED$_{50}$ value was determined by plotting the percent of control (number of plaques in untreated cells) versus the number of plaques in cells at the tested drug concentrations. Those values appear in Table I, below.

Results

The present helioxanthin compounds have demonstrated activity against hepatitis B virus, anti-flavivirus such as the Yellow Fever virus and HSV activity. Helioxanthin Nos. 145 and its analogs No. 135-1, No. 122-1 and No. 156 all could inhibit HBV replication and HbsAg expression. However, Helioxanthin No. 145 was the most active compound in the series tested.

Additionally, No. 145 and its analog 157 also demonstrated activity against the Yellow fever virus. However, No. 145 alone showed anti-HSV activity in the HSV-I, HSV-II and HSV TK minus strain.

It is to be understood by those skilled in the art that the foregoing description and examples are illustrative of practicing the present invention, but are in no way limiting. Variations of the detail presented herein may be made without departing from the spirit and scope of the present invention as defined by the following claims.

TABLE 1

Anti-viral activity and cytotoxicity of Helioxanthin and its analogues

| Compound | Anti-viral activity ($ED_{50}$) ($\mu M$) | | | Cytotoxicity ($IC_{50}$) ($\mu M$) | | Solubility* ($\mu M$) |
| --- | --- | --- | --- | --- | --- | --- |
|  | HbsAg | HBV DNA | YFV | HepG2 cell | CEM cell |  |
| 145 (ZHU-IX-139-1)(11) | 4 | 1 | 9.5 | 26 | 22 | 24.7 |
| ZHU-IX-139-2 (10) | 10 (60%) | >10 | 16 | 12 | 18 | 21 |
| ZHU-IX-143 (20) | >10 | >10 | >10 | 20 | >30 | 11.9 |
| ZHU-IX-124-2 (9) | 10 (70%) | 10 | >10 | 16 | >30 | 127.2 |
| ZHU-IX-135-1 (8) | 8.5 | 3 | 14 | 12 | >30 | 24.8 |
| ZHU-IX-122-1 (12) | 10 (60%) | 5 | >10 | >30 | >30 | 52.9 |
| ZHU-IX-120-1 (5) | >10 | >10 | >10 | 6 | >30 | 13.8 |
| ZHU-IX-120-2 (6) | >10 | >10 | >10 | 6 | >30 | 13.1 |
| ZHU-IX-120-3 | >10 | >10 | >10 | 11 | >30 | 11.8 |
| ZHU-IX-157 (18) | 10 | 2.5 | 8 | 26 | >30 | 255 |
| ZHU-IX-153 (19) | >10 | >10 | >10 | >30 | — | 255 |
| ZHU-IX-159 (17) | 10 (70%) | >10 | >10 | 16 | — | 24.4 |
| ZHU-IX-163-2 (16) | >10 | >10 | >10 | 17 | — | 18.4 |
| ZHU-IX-189 (13) | >10 | >10 | >25 | — | — | — |
| ZHU-X-4 (14) | >10 | >10 | >20 | — | — | — |
| ZHU-X-10 (15) | >10 | >10 | >25 | — | — | — |

NOTE:
1. Compound No. 145 was tested against HSV-1, HSV-II and HSV-I TK strain and the $ED_{50}$ were 1.1, 1.8 and 8.5 $\mu M$, respectively.
2. Compound Nos. 139-2, 143, 124-2, 135-1, 122-1, 120-1, 120-2, 120-3, 189 and X-4 were found inactive against HSV-I and HSV-II.
3. The symbol "*" denotes the concentration of the saturated solution in PBS at room temperature.
4. Each bold number references the compound as shown in the synthesis reactions of Scheme 1. (e.g., 145 (ZHU-IX-139-1) is Compound (11)).

Biological testing results of Helioxanthin and its derivatives for suppression of HBsAg in HepA2 and Hep3B cells in serum-free condition for 2 days

| Compound | $EC_{50}$ ** ($\mu M$) | |
| --- | --- | --- |
|  | HepA2 | Hep3B |
| Helioxanthin | 0.250 | 0.025 |
| Taiwanin C | 1.250 | 1.000 |
| Diphylline | —(***) | — |
| Taiwanin E | — | — |
| Taiwanin E acetate | — | — |
| Dehydroconidendrin Diacetate | — | — |
| Conidendrin | — | — |
| Conidendrin Diacetate | — | — |
| Conidendrin Methyl Ether | — | — |
| Dehydroconidendrin | — | — |
| No. 294 | — | — |
| No. 48 | — | — |
| No. 45 | — | — |
| Diphylline Acetate | — | — |
| Justicidin A | — | — |

The symbol, "*" denotes HepA2, HBV DNA stable transfected HBV dimer DNA.
The symbol, "**" denotes $EC_{50}$, the concentration of tested compounds which exerted 50% reduction of HBsAg secretion in human hepatoma cells.
The symbol "***" denotes that the supression of HBsAg secretion was not detected relative to non-treated cells or where the concentration was greater than 12.5 $\mu M$.

What is claimed is:

1. A pure compound according to the structure:

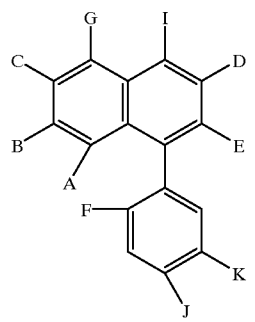

I

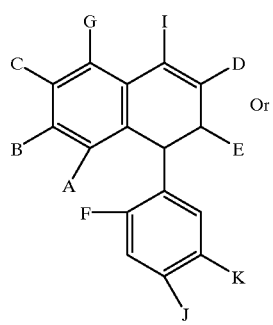

II

Or

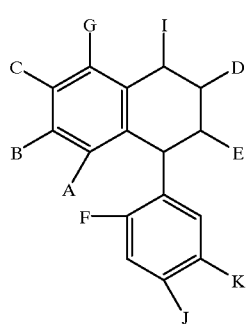

III where A is H, OH, OR or forms a 1,3 dioxolane group with B such that A and B are O and are bridged together by a —CH$_2$— group;
C is H, OH, OR or forms a 1,3 dioxolane group with B such that B and C are O and are bridged together by a —CH$_2$— group;
B is OH, OR or forms a 1,3 dioxolane group with either A or C;
R is a C$_1$ to C$_3$ alkyl group, benzyl group or a C$_1$ to C$_{20}$ acyl group;
D and E are the same or different and are selected from CH$_3$, CH$_2$OH, CH$_2$OR, CHO, COOH or a pharmaceutically acceptable salt thereof, CH$_2$COOR$^1$ or a keto group or —CH$_2$— group, with the proviso that when D or E is a keto group, the other of D or E is a keto group or a methylene group and D and E are linked together by an —O— group to form a five-membered lactone ring or a dicarboxylic acid anhydride ring and with the further proviso that when B and A form a 1,3 dioxolane ring and when J and K form a 1,3, dioxolane ring, D and E do not form a lactone group where D is a keto group and E is a methylene group;
R$^1$ is a C$_1$ to C$_3$ alkyl group;
F and G are H or Br;
I is H, OH, OR or Br and
J and K are the same or different and are selected from CH$_3$, CH$_2$OH, CH$_2$OR, CHO, COOH or a pharmaceutically acceptable salt thereof or together form a 1,3 dioxolane ring such that J and K are O and are bridged by a —CH$_2$— group.

2. The compound according to claim 1, structure I, wherein G and F are Br.

3. The compound according to claim 1, structure I, wherein C, F and I are H, G is Br, A and B together form a 1,3 dioxolane group, J and K together form a 1,3 dioxolane group and D and E are each CH$_2$OH groups.

4. The compound according to claim 1, structure I, wherein C, F, G and I are H, A and B together form a 1,3 dioxolane group, J and K together form a 1,3 dioxolane group, D is a CH$_2$OH group and E is a CH$_3$ group.

5. The compound according to claim 1, structure I, wherein C, F, G and I are H, A and B together form a 1,3 dioxolane group, J and K together form a 1,3 dioxolane group, D is a COO$^-$ Na+ group and E is a CH$_2$OH group.

6. The compound according to claim 1, structure I, wherein A, F, G and I are H, B and C together form a 1,3 dioxolane group, D is a methylene group, E is a keto group and D and E are linked together through an —O— to form a five-membered lactone ring and J and K together form a 1,3 dioxolane group.

7. A method of treating a patient for a viral infection selected from the group consisting of Hepatitis B virus, Hepatitis C virus, Yellow Fever, Dengue Virus, Japanese Encephalitis and West Nile virus comprising administering to said patient an effective amount of a compound according to the structure:

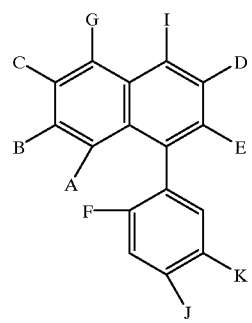

I

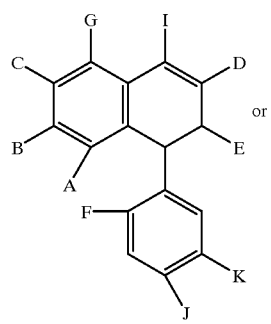

II or

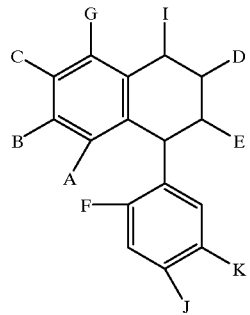

III where A is H, OH, OR or forms a 1,3 dioxolane group with B such that A and B are O and are bridged together by a —CH$_2$— group;

C is H, OH, OR or forms a 1,3 dioxolane group with B such that B and C are O and are bridged together by a —CH$_2$— group;

B is OH, OR or forms a 1,3 dioxolane group with either A or C;

R is a C$_1$ to C$_3$ alkyl group or a C$_1$ to C$_{20}$ acyl group;

D and E are the same or different and are selected from CH$_3$, CH$_2$OH, CH$_2$OR, CHO, COOH or a pharmaceutically acceptable salt thereof, CH$_2$COOR$^1$ or a keto group or —CH$_2$— group, with the proviso that when D or E is a keto group, the other of D or E is a keto group or a methylene group and D and E are linked together by an —O— group to form a five-membered lactone ring or a dicarboxylic acid anhydride ring;

R$^1$ is a C$_1$ to C$_3$ alkyl group;

F and G are H or Br;

I is H, OH, OR or Br and

J and K are the same or different and are selected from CH$_3$, CH$_2$OH, CH$_2$OR, CHO, COOH, COO$^-$ Na$^+$ or together form a 1,3 dioxolane ring such that J and K are O and are bridged by a —CH$_2$— group.

8. The method according to claim 7 wherein said virus is HBV or Yellow Fever virus and wherein said compound is according to structure I, wherein G and F are Br.

9. The method according to claim 7 wherein said virus is Hepatitis B virus, Hepatitis C virus or Yellow Fever virus and wherein said compound is according to structure I, wherein C, F, G and I are H, A and B form a 1,3 dioxolane ring, D is a keto group, E is a methylene group and D and E are linked together by an —O— to form a five-membered lactone ring and J and K together form a 1,3 dioxolane ring.

10. The method according to claim 7, wherein said virus is Hepatitis B virus, Hepatitis C virus or Yellow Fever virus and wherein said compound is according to structure I, wherein C, F and I are H, G is Br, A and B together form a 1,3 dioxolane group, J and K together form a 1,3 dioxolane group and D and E are each CH$_2$OH groups.

11. The method according to claim 7, wherein said virus is Hepatitis B virus, Hepatitis C virus or Yellow Fever virus and wherein said compound is according to structure I, wherein C, F, G and I are H, A and B together form a 1,3 dioxolane group, J and K together form a 1,3 dioxolane group, D is a CH$_2$OH group and E is a CH$_3$ group.

12. The method according to claim 7, wherein said virus is Hepatitis B virus, Hepatitis C virus or Yellow Fever virus and wherein said compound is according to structure I, wherein C, F, G and I are H, A and B together form a 1,3 dioxolane group, J and K together form a 1,3 dioxolane group, D is a COO$^-$ Na+ group and E is a CH$_2$OH group.

13. The method according to claim 7, wherein said virus is Hepatitis B virus, Hepatitis C virus or Yellow Fever Virus and wherein said compound is according to structure I, wherein A, F, G and I are H, B and C together form a 1,3 dioxolane group, D is a methylene group, E is a keto group and D and E are linked together through an —O— to form a five-membered lactone ring and J and K together form a 1,3 dioxolane group.

14. A pharmaceutical composition for use in treating a virus infection comprising an anti-viral effective amount of at least one compound according to the structure:

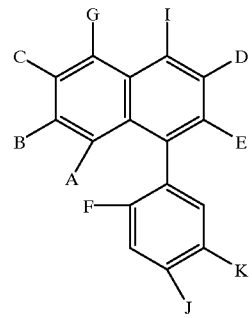

I

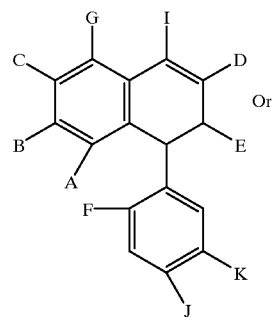

II Or

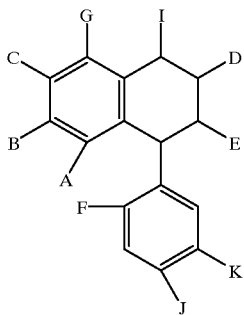

III where A is H, OR or forms a 1,3 dioxolane group with B such that A and B are O and are bridged together by a —CH$_2$— group;

C is H, OH, OR or forms a 1,3 dioxolane group with B such that B and C are O and are bridged together by a —CH$_2$— group;

B is OH, OR or forms a 1,3 dioxolane group with either A or C;

R is a C$_1$ to C$_3$ alkyl group, a benzyl group or a C$_1$ to C$_{20}$ acyl group;

D and E are the same or different and are selected from CH$_3$, CH$_2$OH, CH$_2$OR, CHO, COOH or a pharmaceutically acceptable salt thereof, CH$_2$COOR$^1$ or a keto group or —CH$_2$— group, with the proviso that when D or E is a keto group, the other of D or E is a keto group or a methylene group and D and E are linked together by an —O— group to form a five-membered lactone ring or a dicarboxylic acid anhydride ring;

R$^1$ is a C$_1$ to C$_3$ alkyl group;

F and G are H or Br;

I is H, OH, OR or Br and

J and K are the same or different and are selected from CH$_3$, CH$_2$OH, CH$_2$OR, CHO, COOH or a pharmaceutically acceptable salt thereof, or together form a 1,3 dioxolane ring such that J and K are O and are bridged by a —CH$_2$— (methylene) group, optionally in combination with a pharmaceutically acceptable excipient, carrier or additive.

15. The composition according to claim 14, wherein said compound is according to structure I, wherein G and F are Br.

16. The composition according to claim 14, wherein said compound is according to structure I, wherein C, F, G and I are H, A and B form a 1,3 dioxolane ring, D is a keto group, E is a methylene group and D and E are linked together by an —O— to form a five-membered lactone ring and J and K together form a 1,3 dioxolane ring.

17. The composition according to claim 14, wherein said compound is according to structure I, wherein C, F and I are H, G is Br, A and B together form a 1,3 dioxolane group, J and K together form a 1,3 dioxolane group and D and E are each CH$_2$OH groups.

18. The composition according to claim 14, wherein said compound is according to structure I, wherein C, F, G and I are H, A and B together form a 1,3 dioxolane group, J and K together form a 1,3 dioxolane group, D is a CH$_2$OH group and E is a CH$_3$ group.

19. The composition according to claim 14, wherein said compound is according to structure I, wherein C, F, G and I are H, A and B together form a 1,3 dioxolane group, J and K together form a 1,3 dioxolane group, D is a COO$^-$ Na+ group and E is a CH$_2$OH group.

20. The composition according to claim 14, wherein said compound is according to structure I, wherein A, F, G and I are H, B and C together form a 1,3 dioxolane group, D is a methylene group, E is a keto group and D and E are linked together through an —O— to form a five-membered lactone ring and J and K together form a 1,3 dioxolane group.

21. A method of preventing a virus infection in a patient, said virus being selected from the group consisting of Hepatitis B virus, Hepatitis C virus, Yellow Fever virus, Dengue Virus, Japanese Encephalitis virus and West Nile virus comprising administering to said patient in need thereof an effective amount of a compound according to the structure:

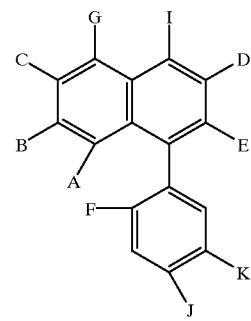

I

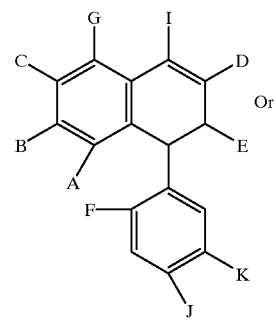

II

Or

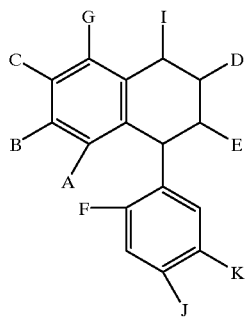

III where A is H, OR or forms a 1,3 dioxolane group with B such that A and B are O and are bridged together by a —CH$_2$— group;

C is H, OH, OR or forms a 1,3 dioxolane group with B such that B and C are O and are bridged together by a —CH$_2$— group;

B is OH, OR or forms a 1,3 dioxolane group with either A or C;

R is a C$_1$ to C$_3$ alkyl group, a benzyl group or a C$_1$ to C$_{20}$ acyl group D and E are the same or different and are selected from CH$_3$, CH$_2$OH, CH$_2$OR, CHO, COOH or a pharmaceutically acceptable salt thereof, CH$_2$COOR$^1$ or a keto group or —CH$_2$— group, with the proviso that when D or E is a keto group, the other of D or E is a keto group or a methylene group and D and E are linked together by an —O— group to form a five-membered lactone ring or a dicarboxylic acid anhydride ring;

R$^1$ is a C$_1$ to C$_3$ alkyl group;

F and G are H or Br;

I is H, OH, OR or Br and

J and K are the same or different and are selected from CH$_3$, CH$_2$OH, CH$_2$OR, CHO, COOH or a pharmaceutically acceptable salt thereof, or together form a 1,3 dioxolane ring such that J and K are O and are bridged by a —CH$_2$— group, optionally in combination with a pharmaceutically acceptable excipient, carrier or additive.

22. The method according to claim 21 wherein said virus is Hepatitis B virus, Hepatitis C virus or Yellow Fever virus and wherein said compound is according to structure I, wherein G and F are Br.

23. The method according to claim 21 wherein said virus is Hepatitis B virus, Hepatitis C virus or Yellow Fever virus and wherein said compound is according to structure I, wherein C, F, G and I are H, A and B form a 1,3 dioxolane ring, D is a keto group, E is a methylene group and D and E are linked together by an —O— to form a five-membered lactone ring and J and K together form a 1,3 dioxolane ring.

24. The method according to claim 21, wherein said virus is Hepatitis B virus, Hepatitis C virus or Yellow Fever virus and wherein said compound is according to structure I, wherein C, F and I are H, G is Br, A and B together form a 1,3 dioxolane group, J and K together form a 1,3 dioxolane group and D and E are each CH$_2$OH groups.

25. The method according to claim 21, wherein said virus is Hepatitis B virus, Hepatitis C virus or Yellow Fever virus and wherein said compound is according to structure I, wherein C, F, G and I are H, A and B together form a 1,3 dioxolane group, J and K together form a 1,3 dioxolane group, D is a CH$_2$OH group and E is a CH$_3$ group.

26. The method according to claim 21, wherein said virus is Hepatitis B virus, Hepatitis C virus or Yellow Fever virus and wherein said compound is according to structure I, wherein C, F, G and I are H, A and B together form a 1,3 dioxolane group, J and K together form a 1,3 dioxolane group, D is a COO$^-$ Na+ group and E is a CH$_2$OH group.

27. The method according to claim 21, wherein said virus is Hepatitis B virus, Hepatitis C virus or Yellow Fever Virus and wherein said compound is according to structure I, wherein A, F, G and I are H, B and C together form a 1,3 dioxolane group, D is a methylene group, E is a keto group and D and E are linked together through an —O— to form a five-membered lactone ring and J and K together form a 1,3 dioxolane group.

28. A method of preventing a hepatoma secondary to a Hepatitis B or Hepatitis C virus infection in a patient, said method comprising administering to said patient in need thereof an effective amount of a compound according to the structure:

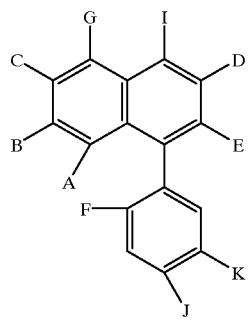

I

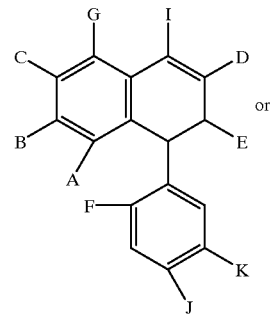

II or

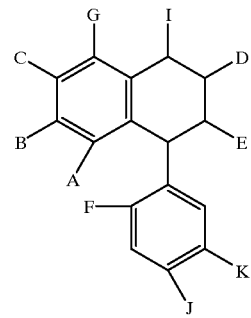

III where A is H, OR or forms a 1,3 dioxolane group with B such that A and B are O and are bridged together by a —CH$_2$— group;

C is H, OH, OR or forms a 1,3 dioxolane group with B such that B and C are O and are bridged together by a —CH$_2$— group;

B is OH, OR or forms a 1,3 dioxolane group with either A or C;

R is a C$_1$ to C$_3$ alkyl group, a benzyl group or a C$_1$ to C$_{20}$ acyl group D and E are the same or different and are selected from CH$_3$, CH$_2$OH, CH$_2$OR, CHO, COOH or a pharmaceutically acceptable salt thereof, CH$_2$COOR$^1$ or a keto group or —CH$_2$— group, with the proviso that when D or E is a keto group, the other of D or E is a keto group or a methylene group and D and E are linked together by an —O— group to form a five-membered lactone ring or a dicarboxylic acid anhydride ring;

R$^1$ is a C$_1$ to C$_3$ alkyl group;

F and G are H or Br;

I is H, OH, OR or Br and

J and K are the same or different and are selected from CH$_3$, CH$_2$OH, CH$_2$OR, CHO, COOH or a pharmaceutically acceptable salt thereof, or together form a 1,3 dioxolane ring such that J and K are O and are bridged by a —CH$_2$— group, optionally in combination with a pharmaceutically acceptable excipient, carrier or additive.

29. The method according to claim 28 wherein said compound is according to structure I, wherein G and F are Br.

30. The method according to claim 28 wherein said compound is according to structure I, wherein C, F, G and I are H, A and B form a 1,3 dioxolane ring, D is a keto group, E is a methylene group and D and E are linked together by an —O— to form a five-membered lactone ring and J and K together form a 1,3 dioxolane ring.

31. The method according to claim 28, wherein said compound is according to structure I, wherein C, F and I are H, G is Br, A and B together form a 1,3 dioxolane group, J and K together form a 1,3 dioxolane group and D and E are each CH₂OH groups.

32. The method according to claim 28, wherein said compound is according to structure I, wherein C, F, G and I are H, A and B together form a 1,3 dioxolane group, J and K together form a 1,3 dioxolane group, D is a CH₂OH group and E is a CH₃ group.

33. The method according to claim 28, wherein said compound is according to structure I, wherein C, F, G and I are H, A and B together form a 1,3 dioxolane group, J and K together form a 1,3 dioxolane group, D is a COO⁻ Na+ group and E is a CH₂OH group.

34. The method according to claim 28, wherein said virus is Hepatitis B virus, Hepatitis C virus or Yellow Fever Virus and wherein said compound is according to structure I, wherein A, F, G and I are H, B and C together form a 1,3 dioxolane group, D is a methylene group, E is a keto group and D and E are linked together through an —O— to form a five-membered lactone ring and J and K together form a 1,3 dioxolane group.

35. The method according to claim 7 wherein said viral infection is a 3TC-resistant Hepatitis B virus infection.

36. The method according to claim 9 wherein said viral infection is a 3TC-resistant Hepatitis B virus infection.

37. A pharmaceutical composition comprising an antiviral effective amount of at least one compound according to the structure:

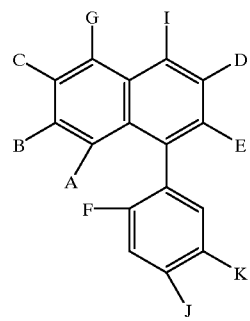

where C, G, F and I are H;

A is O and B is O such that A and B are bridged together by a —CH₂— group to form a 1,3-dioxolane group;

J is O and K is O such that J and K are bridged together by a —CH₂— group to form a 1,3-dioxolane group;

D is COOH or a pharmaceutically acceptable salt thereof, or a keto group; and

E is CH₂OH when D is COOH or its pharmaceutically acceptable salt thereof, or a methylene group when D is a keto group such that D and E are linked together by an —O— group to form a five-membered lactone ring, optionally, in combination with a pharmaceutically acceptable excipient carrier or additive.

38. The composition according to claim 37 where D is a keto group and E is a methylene group such that D and E are linked together by an —O— group to form a five-membered lactone ring.

39. A method of treating a patient for a viral infection selected from the group consisting of Hepatitis B virus, Hepatitis C virus, Yellow Fever, Dengue Virus, Japanese Encephalitis, West Nile virus comprising administering to said patient an effective amount of a compound according to the structure:

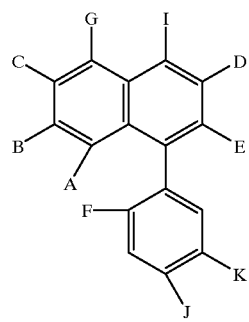

where C, G, F and I are H;

A is O and B is O such that A and B are bridged together by a —CH₂— group to form a 1,3-dioxolane group;

J is O and K is O such that J and K are bridged together by a —CH₂— group to form a 1,3-dioxolane group;

D is COOH or a pharmaceutically acceptable salt thereof, or a keto group; and

E is CH₂OH when D is COOH or its pharmaceutically acceptable salt thereof, or a methylene group when D is a keto group such that D and E are linked together by an —O— group to form a five-membered lactone ring, optionally, in combination with a pharmaceutically acceptable excipient carrier or additive.

40. The method according to claim 39 where D is a keto group and E is a methylene group such that D and E are linked together by an —O— group to form a five-membered lactone ring.

41. The method according to claim 40 wherein said virus is Hepatitis C virus.

42. The method according to claim 40 wherein said virus is Hepatitis B virus.

43. The method according to claim 40 wherein said virus is 3TC resistant Hepatitis B virus.

44. A method of preventing a virus infection in a patient, said virus being selected from the group consisting of Hepatitis B virus, Hepatitis C virus, Yellow Fever virus, Dengue Virus, Japanese Encephalitis virus and West Nile virus comprising administering to said patient in need thereof an effective amount of a compound according to the structure:

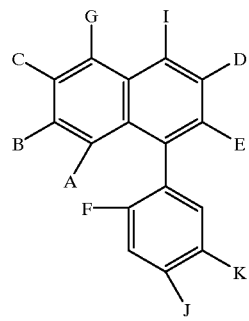

where C, G, F and I are H;

A is O and B is O such that A and B are bridged together by a —CH₂— group to form a 1,3-dioxolane group;

J is O and K is O such that J and K are bridged together by a —CH$_2$— group to form a 1,3-dioxolane group;

D is COOH or a pharmaceutically acceptable salt thereof, or a keto group; and

E is CH$_2$OH when D is COOH or its pharmaceutically acceptable salt thereof, or a methylene group when D is a keto group such that D and E are linked together by an —O— group to form a five-membered lactone ring, optionally, in combination with a pharmaceutically acceptable excipient carrier or additive.

45. The method according to claim 44 where D is a keto group and E is a methylene group such that D and E are linked together by an —O— group to form a five-membered lactone ring.

46. The method according to claim 45 wherein said virus is Hepatitis C virus.

47. The method according to claim 45 wherein said virus is Hepatitis B virus.

48. The method according to claim 47 wherein said virus is 3TC resistant.

49. A method of preventing a hepatoma secondary to a Hepatitis B or Hepatitis C virus infection in a patient, said method comprising administering to said patient in need thereof an effective amount of a compound according to the structure:

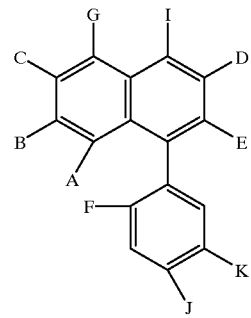

where C, G, F and I are H;

A is O and B is O such that A and B are bridged together by a —CH$_2$— group to form a 1,3-dioxolane group;

J is O and K is O such that J and K are bridged together by a —CH$_2$— group to form a 1,3-dioxolane group;

D is COOH or a pharmaceutically acceptable salt thereof, or a keto group; and

E is CH$_2$OH when D is COOH or its pharmaceutically acceptable salt thereof, or a methylene group when D is a keto group such that D and E are linked together by an —O— group to form a five-membered lactone ring, optionally, in combination with a pharmaceutically acceptable excipient carrier or additive.

50. The method according to claim 49 where D is a keto group and E is a methylene group such that D and E are linked together by an —O— group to form a five-membered lactone ring.

51. The method according to claim 49 wherein said virus is Hepatitis C virus.

* * * * *